US012673136B2

(12) United States Patent　　(10) Patent No.: US 12,673,136 B2
Borden　　(45) Date of Patent: Jul. 7, 2026

(54) ENHANCED OSTEOINDUCTIVE COMPOSITIONS, SYSTEMS, AND METHODS OF MANUFACTURE

(71) Applicant: ORBIO INNOVATIONS, LLC, Boulder, CO (US)

(72) Inventor: Mark D. Borden, Boulder, CO (US)

(73) Assignee: ORBIO INNOVATIONS, LLC, Boulder, CO (US)

( * ) Notice: Subject to any disclaimer, the term of this patent is extended or adjusted under 35 U.S.C. 154(b) by 0 days.

(21) Appl. No.: 19/209,618

(22) Filed: May 15, 2025

(65) Prior Publication Data

US 2025/0352696 A1　　Nov. 20, 2025

Related U.S. Application Data

(60) Provisional application No. 63/647,769, filed on May 15, 2024.

(51) Int. Cl.
| | |
|---|---|
| *A61L 27/36* | (2006.01) |
| *A61K 35/32* | (2015.01) |
| *A61L 27/54* | (2006.01) |

(52) U.S. Cl.
CPC .......... *A61L 27/3608* (2013.01); *A61K 35/32* (2013.01); *A61L 27/3691* (2013.01); *A61L 27/54* (2013.01); *A61L 2430/02* (2013.01)

(58) Field of Classification Search
None
See application file for complete search history.

(56) References Cited

U.S. PATENT DOCUMENTS

| | | |
|---|---|---|
| 7,132,110 B2 | 11/2006 | Kay et al. |
| 7,811,608 B2 | 10/2010 | Kay et al. |

| | | | |
|---|---|---|---|
| 2003/0044445 A1* | 3/2003 | Kay | ...................... A61L 27/365 |
| | | | 424/549 |
| 2010/0166879 A1 | 7/2010 | Shim et al. | |
| 2012/0258178 A1 | 10/2012 | Benham et al. | |
| 2014/0255506 A1 | 9/2014 | Behnam et al. | |
| 2021/0069380 A1 | 3/2021 | McGraw et al. | |

OTHER PUBLICATIONS

Song et al, Cell Tissue Bank, 2023, vol. 24: 203-210. (Year: 2023).*
Syftestad et al., "Degradation of Bone Matrix Morphogenetic Activity by Pulverization," Clinical Orthopaedics and Related Research, No. 141, Jun. 1979, pp. 281-286.
Vail et al., "Equine Demineralized Bone Matrix: Relationship Between Particle Size and Osteoinduction," Veterinary Surgery 23:386-395, 1994.
Zhang et al., "Effect(s) of the Demineralization Process on the Osteoinductivity of Demineralized Bone Matrix," J Periodontal, Nov. 1997;68:1085-1092.

* cited by examiner

*Primary Examiner* — Allison M Fox
(74) *Attorney, Agent, or Firm* — NORTON ROSE FULBRIGHT US LLP

(57) ABSTRACT

An enhanced osteoinductive composition is prepared by subjecting particulate bone to a demineralization process that is optimized based on the particle size. In broad particle size ranges, ground bone is separated by particle size and each size range is subjected to independent demineralization conditions that maintain high levels of endogenous growth factors found in bone. Following demineralization, the size ranges are recombined to create an enhanced osteoinductive composition. In narrow particle size ranges, bone is milled to achieve a predetermined size, and the demineralization process is adjusted to this size range. Size-optimized demineralization is also used to create enhanced demineralized bone matrix particles in the size range of <125 μm. Enhanced osteoinductive compositions using size-optimized demineralization bone matrix and protein isolation and/or bone gelatin creation techniques are disclosed. Tissue repair compositions using the enhanced osteoinductive particles are also disclosed.

3 Claims, 14 Drawing Sheets

200

302

STEP 1. BONE IS SUBJECTED TO A PREGRINDING PROCESS TO CREATE CHUNKS OF BONE <8mm (EXAMPLE SHOWING COW BONE)

304

STEP 2. BONE CHUNKS ARE PLACED IN A MILLING CONTAINER WITH A STAINLESS STEEL MILLING BALL, COOLED IN LIQUID NITROGEN, AND THEN SHAKEN TO PULVERIZE THE FROZEN BONE.

306

STEP 3. BONE IS REMOVED FROM THE MILL; A FINE PARTICLE POWDER IS OBSERVED (90% OF PARTICLES <50μm)

202

CORTICAL BONE AFTER CRYOMILLING

CORTICAL BONE BEFORE CRYOMILLING

GROWTH FACTOR PEPTIDE WITH "COTTON-LIKE" APPEARANCE

DRY DBM FIBERS

DBM FIBERS SOAKED IN GROWTH FACTOR PEPTIDE SOLUTION

FREEZE-DRIED ENHANCED DBM FIBERS (DBM FIBERS +GROWTH FACTOR PEPTIDE)

HANDLING OF ENHANCED DBM FIBERS FOLLOWING HYDRATION

FREEZE-DRIED ENHANCED DBM PUTTY (SIZE-OPTIMIZED DBM PARTICLES + GROWTH FACTOR PEPTIDE)

HANDLING OF ENHANCED DBM PUTTY FOLLOWING HYDRATION

FREEZE-DRIED GROWTH FACTOR PEPTIDE FOAM

200

ENHANCED DBM PUTTY (SIZE-OPTIMIZED DBM PARTICLES + PHOSPHOLIPID CARRIER)

1200

ENHANCED OSTEOINDUCTIVE COMPOSITIONS, SYSTEMS, AND METHODS OF MANUFACTURE

CROSS-REFERENCE TO RELATED APPLICATIONS

This application claims the benefit of priority of U.S. Provisional Patent Application No. 63/647,769, filed May 15, 2024, which is hereby incorporated by reference in its entirety.

FIELD

The present application relates to implantable tissue repair compositions and methods to manufacture such compositions.

BACKGROUND

Human allograft bone is commonly used as a bone graft material for orthopedic and spine surgery where bone regeneration is needed. Bone is a biological composite composed of a calcium phosphate mineral phase and an organic phase consisting of collagen and a variety of other non-collagenous proteins. Allograft tissues derived from cortical and cancellous bone from tissue donors are used as bone grafts. These grafts can be in a mineralized form or a demineralized form, where the bone mineral is removed [e.g., demineralized bone matrix (DBM)]. While all allograft bone forms support new bone formation on the surface of the graft (e.g., osteoconduction), the demineralized bone has additional properties that are advantageous to bone healing. The non-collagenous proteins found in DBM include a variety of growth factor proteins (e.g., BMP 2, BMP-4, BMP-7, TBF-B, VEGF, FGF, PDGF, etc.) that have been shown to accelerate and positively influence the bone healing process. These osteoinductive (OI) proteins are capable of stimulating osteoblast function, differentiating stem cells into osteoblasts, and acting as signaling molecules that aid in the bone formation process. However, in mineralized bone, these proteins are trapped within a mineral-collagen fiber matrix and are unable to diffuse out of the tissue and interact with local cells to stimulate a healing response. As such, mineralized bone allografts function as passive scaffolds for bone formation which cannot actively stimulate a bone healing response.

In order to expose the active OI proteins, bone is subjected to an acid demineralization process to dissolve and remove the bone mineral. Following demineralization, the resulting tissue consists of a naturally cross-linked collagen matrix with embedded OI proteins. With the bone mineral removed, the OI proteins become bioavailable, due to their ability to diffuse out of the collagen matrix when implanted in a bone defect. During healing, the release of growth factors from DBM stimulates a bone healing response. Due to this property, DBM processed from human tissue donors is widely used as a bone graft material in orthopedic and spine surgery. Commercially available DBM products consist of DBM particles in a granule, fiber, or cancellous sponge form. These tissue can be used alone in in combination with a bioabsorbable carrier to form DBM putties and gels.

Although DBM products demonstrate biological activity through their growth factor content, the demineralization process used to create the DBM in these products has a number of shortcomings that reduce the osteoinductive potential of the tissue and limit the use of particles/fibers to specific implant compositions.

It is with these observations in mind, among others, that various aspects of the present disclosure were conceived and developed.

SUMMARY

Aspects of the present disclosure are directed to a method of forming an enhanced demineralized bone matrix (DBM), the method comprising: separating bone particles into at least a first size range and a second size range; and independently demineralizing the bone particles of the first size range and the bone particles of the second size range by using a different demineralization parameter for the first size range than is used for the second size range.

In various aspects, the first size range includes a larger particle size than the second size range, and independently demineralizing the bone particles comprises using: a longer demineralization time for the bone particles of the first size range than the bone particles of the second size range; or a higher acid concentration for the bone particles of the first size range than the bone particles of the second size range; or a stronger type of acid for the bone particles of the first size range than the bone particles of the second size range; or any combination thereof.

In various aspects, the first size range includes a larger particle size than the second size range; and independently demineralizing the bone particles for at least one size range comprises using a two-step process (a first demineralization process and a second demineralization process) that includes using a stronger type of acid for the first demineralization process and using a weaker type of acid for the second demineralization process.

In various aspects, the first size range includes a larger particle size than the second size range; and independently demineralizing the bone particles for at least one size range comprises using a two-step process (a first demineralization process and a second demineralization process) that includes using a strong acid for the first demineralization process and using a weak acid for the second demineralization process.

In various aspects, the first size range is selected from the group consisting of <90 μm, <125 μm, 90 to less than 212 μm, 212 to less than 355 μm, 355 to less than 500 μm, 500 to less than 600 μm, 600 to less than 710 μm, and 710 to less than 850 μm; and the second size range is selected from the group consisting of <90 μm, <125 μm, 90 to less than 212 μm, 212 to less than 355 μm, 355 to less than 500 μm, 500 to less than 600 μm, 600 to less than 710 μm, and 710 to less than 850 μm. For example, in some aspects, the first size range or the second size range is <125 μm.

In various aspects, the methods herein further comprise cryomilling an initial portion of cortical bone material to form the bone particles, the cryomilling comprising cryomilling at <0° C. temperatures by using liquid nitrogen, dry ice, or a freezer, or any combination thereof.

Also provided herein are enhanced demineralized bone matrix (DBM) compositions comprising osteoinductive demineralized bone matrix (DBM) particles wherein the osteoinductive DBM bone particles comprise at least two different size ranges, wherein the first size range comprises a larger particle size than the second size range, wherein each size range is demineralized independently using different demineralization parameters.

In various aspects, the first size range is selected from the group consisting of <90 μm, <125 μm, 90 μm to less than 212 μm, 212 μm to less than 355 μm, 355 μm to less than 500

μm, 500 μm to less than 600 μm, 600 μm to less than 710 μm, and 710 μm to less than 850 μm; and the second size range is selected from the group consisting of <90 μm, <125 μm, 90 μm to less than 212 μm, 212 μm to less than 355 μm, 355 μm to less than 500 μm, 500 μm to less than 600 μm, 600 μm to less than 710 μm, and 710 μm to less than 850 μm. In some aspects, the at least two different size ranges comprise at least one size range of <125 μm.

Also provided herein are tissue repair compositions comprising the enhanced DBM compositions provided herein and a biocompatible carrier. In some aspects, the tissue repair compositions are a moldable putty, an extrudable gel, or a flexible sheet.

Also provided are bone-contacting implants wherein the surface of the bone-contacting implant comprises the enhanced DBM composition disclosed herein.

Also provided are liquid osteoinductive coatings comprising the enhanced DBM composition disclosed herein and an aqueous solution. In various aspects, the aqueous solution may comprise water, a hydrogel, a polymer solution, or a phospholipid solution, or any combination thereof.

Also provided are bone implants comprising a bone contacting implant and a liquid osteoinductive coating disclosed herein. In some aspects, the liquid osteoinductive coating is dried causing the osteoinductive DBM particles to adhere to a surface of the porous bone contacting implant.

Also provided herein are methods of forming a tissue repair composition, the method comprising: separating bone particles into at least a first size range and a second size range; forming a size-optimized demineralized bone matrix (DBM) by independently demineralizing the bone particles of the first size range and the bone particles of the second size range by using a different demineralization parameter for the first size range than is used for the second size range; and combining the DBM with a biocompatible carrier to create the tissue repair composition.

In various aspects, the first size range is <125 μm; and method further comprises producing an osteoinductive growth factor peptide powder from the bone particles in the first size range by: treating the bone particles in the first size range to convert collagen into gelatin; and subsequently drying the bone particles in the first size range to form the osteoinductive growth fact peptide powder.

In various aspects, the first size range is <125 μm, and the method further comprises producing a growth factor peptide solution from the demineralized bone particles of the first size range by: demineralizing the demineralized bone particles of the first size range in a demineralization solution to form a processed demineralization solution, and subjecting the processed demineralization solution to a protein isolation process to create a soluble growth factor solution. In various aspects, the protein isolation process can comprises a dialysis process, a diafiltration process, or a precipitation process. For example, in some aspects, the protein isolation process comprises a dialysis process, or a diafiltration process, and includes a molecular weight cutoff of 10 kDa or less.

In some aspects, the methods herein further comprise creating an osteoinductive growth factor peptide powder by drying the growth factor peptide solution to create the growth factor peptide power.

In some aspects, the methods further comprise mixing the bone particles of the first size range with the growth factor peptide powder disclosed herein.

In various aspects, in the methods herein, the tissue repair composition can be freeze-dried to a rigid form that is designed to be inserted into a musculoskeletal implant. In some aspects, the methods further comprise mixing the bone particles of the first size range with the growth factor peptide powder and freeze-drying the tissue repair composition to a rigid form that is designed to be inserted into a musculoskeletal implant.

Also provided are methods of forming soluble growth factor peptide solution, the method comprising: milling cortical bone to a particle size <125 μm to form a cortical bone powder; demineralizing the cortical bone powder through a first process to form demineralized cortical bone; conducting a second demineralizing on the demineralized cortical bone; and isolating a soluble growth factor peptide solution through a protein purification process.

In various aspects, the protein purification process comprises a dialysis process or a diafiltration process with a molecular weight cut off of 10 kDa or less.

In various aspects, the methods further comprise drying the soluble growth factor peptide solution to form a growth factor peptide powder.

Also provided are soluble growth factor peptide solution formed from any method disclosed herein.

Also provided are growth factor peptide powders formed from any method disclosed herein.

Also provided are tissue repair compositions comprising: a soluble growth factor peptide solution disclosed herein; and cortical bone particles, cancellous bone particles, demineralized bone matrix (DBM) particles, or demineralized bone matrix (DBM) fibers, or any combination thereof, wherein the growth factor peptide solution, growth factor peptide powder, cortical bone particles, cancellous bone particles, DBM particles, and/or DBM fibers are all derived from the same tissue donor.

Also provided are tissue repair compositions comprising: a growth factor peptide powder disclosed herein, and cortical bone particles, cancellous bone particles, demineralized bone matrix (DBM) particles, or demineralized bone matrix (DBM) fibers, or any combination thereof, wherein the growth factor peptide solution, growth factor peptide powder, cortical bone particles, cancellous bone particles, DBM particles, and/or DBM fibers are all derived from the same tissue donor.

Also provided are liquid osteoinductive coatings comprising a soluble growth factor peptide solution disclosed herein and an aqueous solution.

Also provided are liquid osteoinductive coatings comprising the growth factor peptide powder disclosed herein and an aqueous solution.

5

Figure 9:
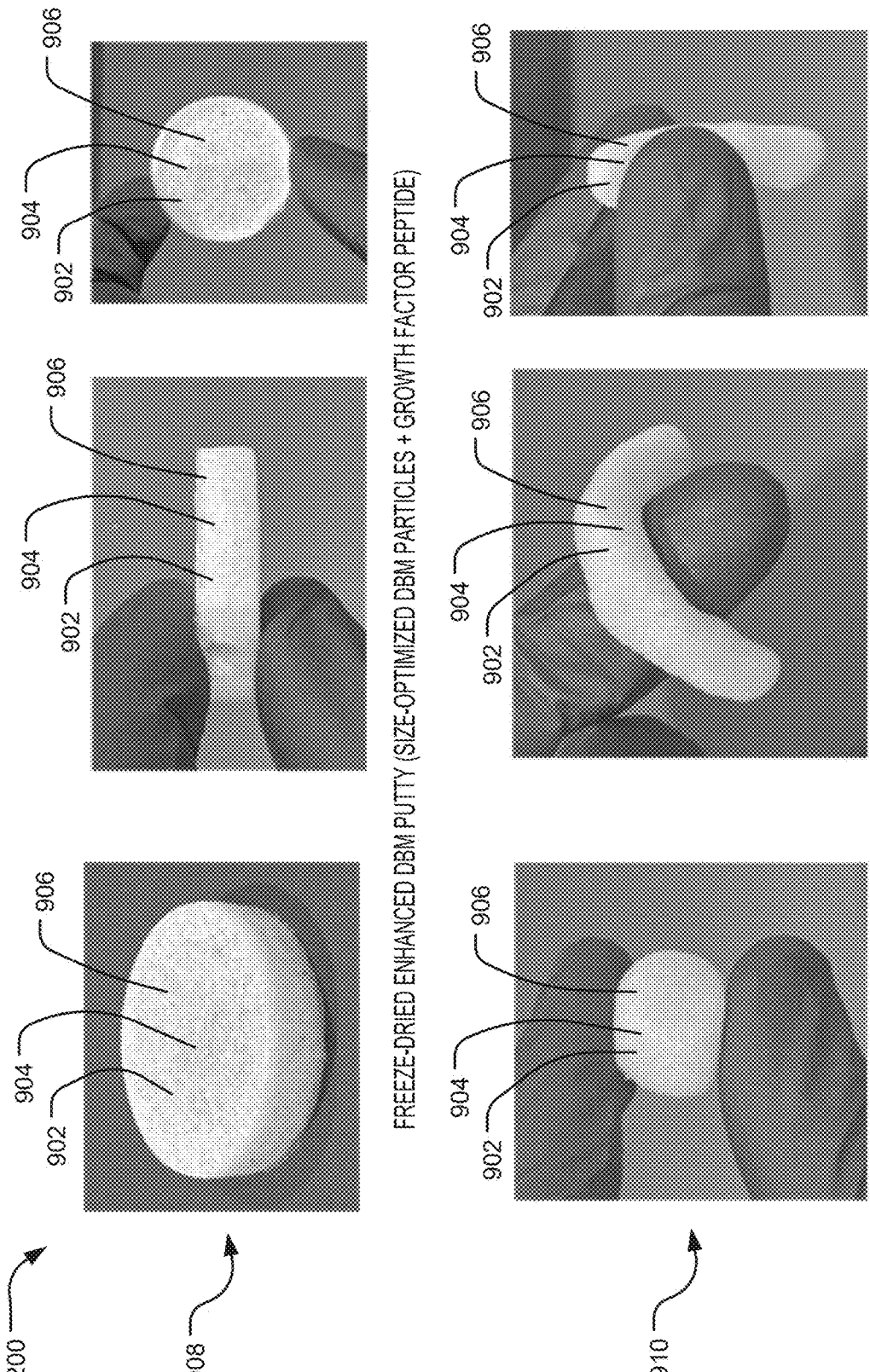

FIG. 9 shows an enhanced DBM putty composed of size-optimized DBM and a growth factor peptide gel.

Figure 10:
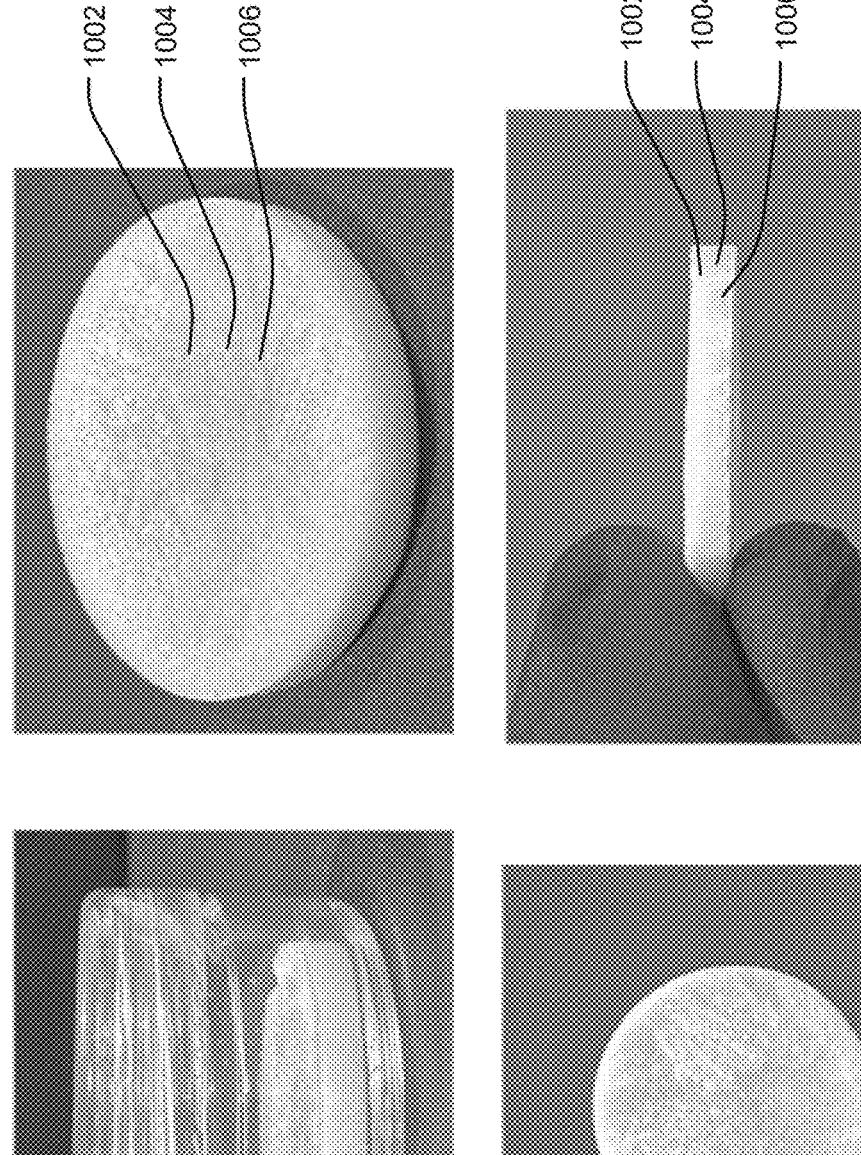

FIG. 10 shows an enhanced osteoinductive composition composed of growth factor peptide.

Figure 11:
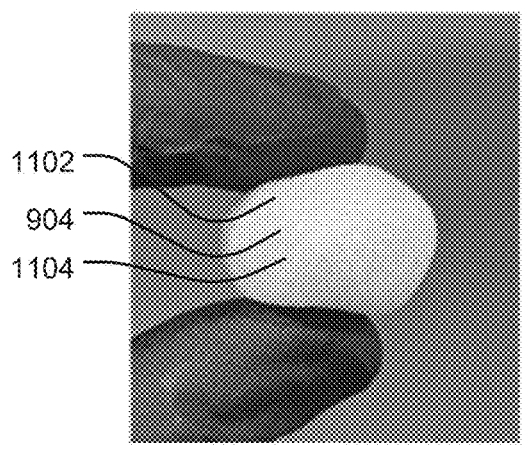
Figure 11:
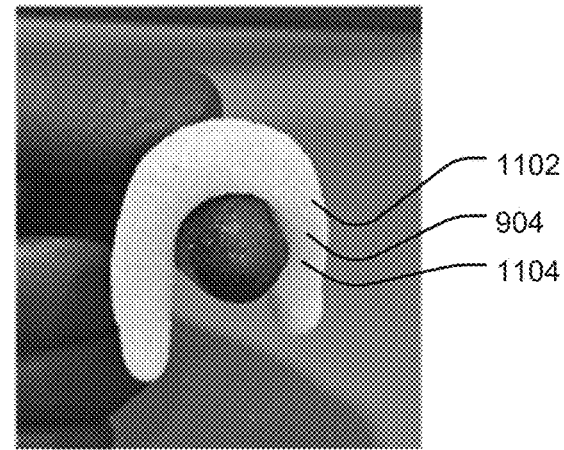
Figure 11:
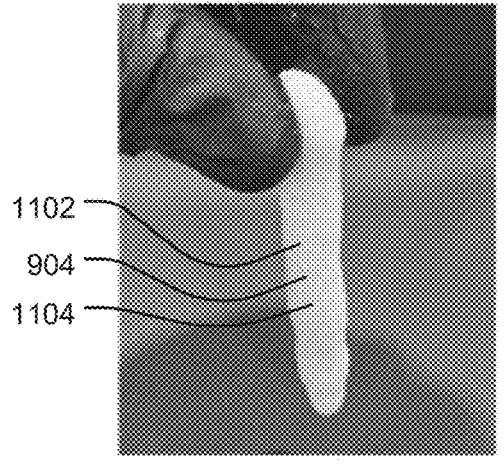
Figure 11:
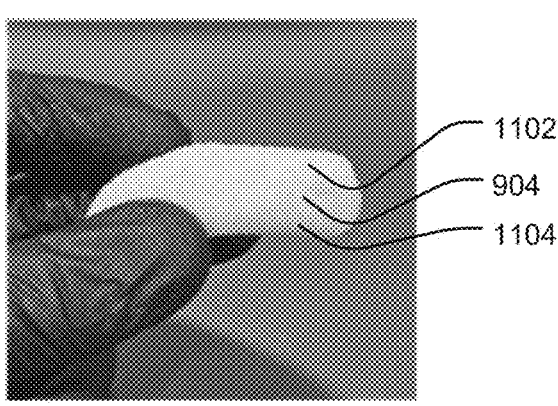

FIG. 11 shows an enhanced DBM putty composed of sized optimized DBM and a phospholipid carrier.

Figure 12:
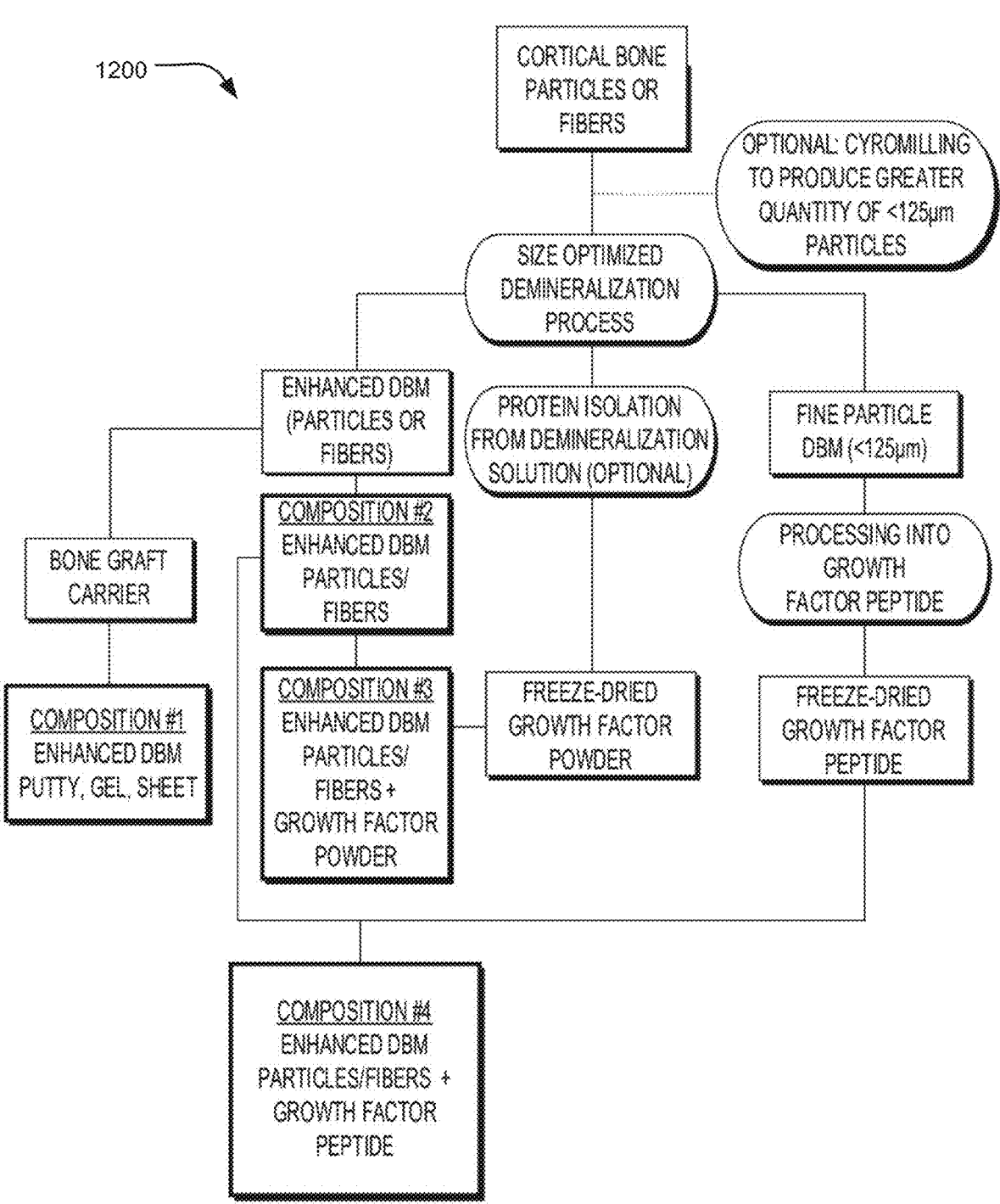

FIG. 12 shows an example method of forming one or more compositions from an enhanced DBM generation procedure.

Figure 13:
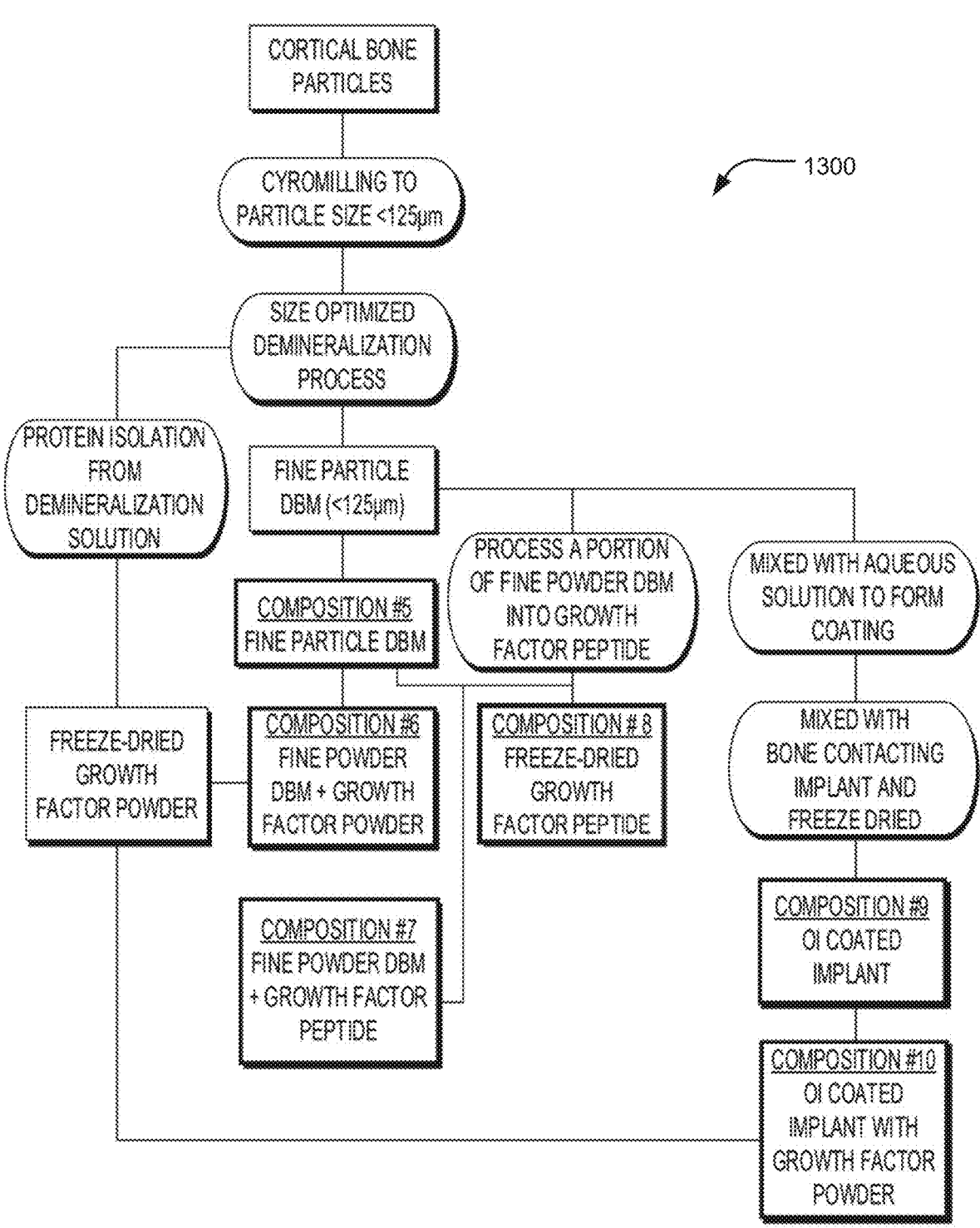

FIG. 13 shows an example method of forming one or more compositions from an enhanced DBM generation procedure.

DETAILED DESCRIPTION

It will be appreciated that numerous specific details are set forth in order to provide a thorough understanding of the examples described herein. However, it will be understood by those of ordinary skill in the art that the examples described herein can be practiced without these specific details. In other instances, methods, procedures, and components have not been described in detail so as not to obscure the related relevant feature being described. Also, the description is not to be considered as limiting the scope of the examples described herein. The drawings are not necessarily to scale, and the proportions of certain parts may be exaggerated to better illustrate details and features of the present disclosure.

The technology disclosed herein can address demineralization issues which occur with a broad particle size range. For instance, most DBM particulate is created from broad particle size range of cortical bone from 125-850 μm. This particle size range purposefully avoids small particles (e.g., <125 μm) which have been shown to have minimal to no growth factor content (e.g., from over-demineralization), and large particles (e.g., >825 μm) that are difficult to fully demineralize (e.g., from under-demineralization). Due to these challenges, the 125-850 μm size range can be considered by some as an optimal particulate size that can be effectively demineralized to residual calcium levels (e.g., <8%) while retaining some of the osteoinductive growth factors in biologically effective amounts. In standard demineralization processes, the bone particles with this broad size range are subjected to a demineralization process using a single acid concentration and a single demineralization duration. One issue with this method is that demineralization is a diffusion-based process where bone mineral is gradually dissolved over time from the outside of the particle to its interior.

Figure 1:
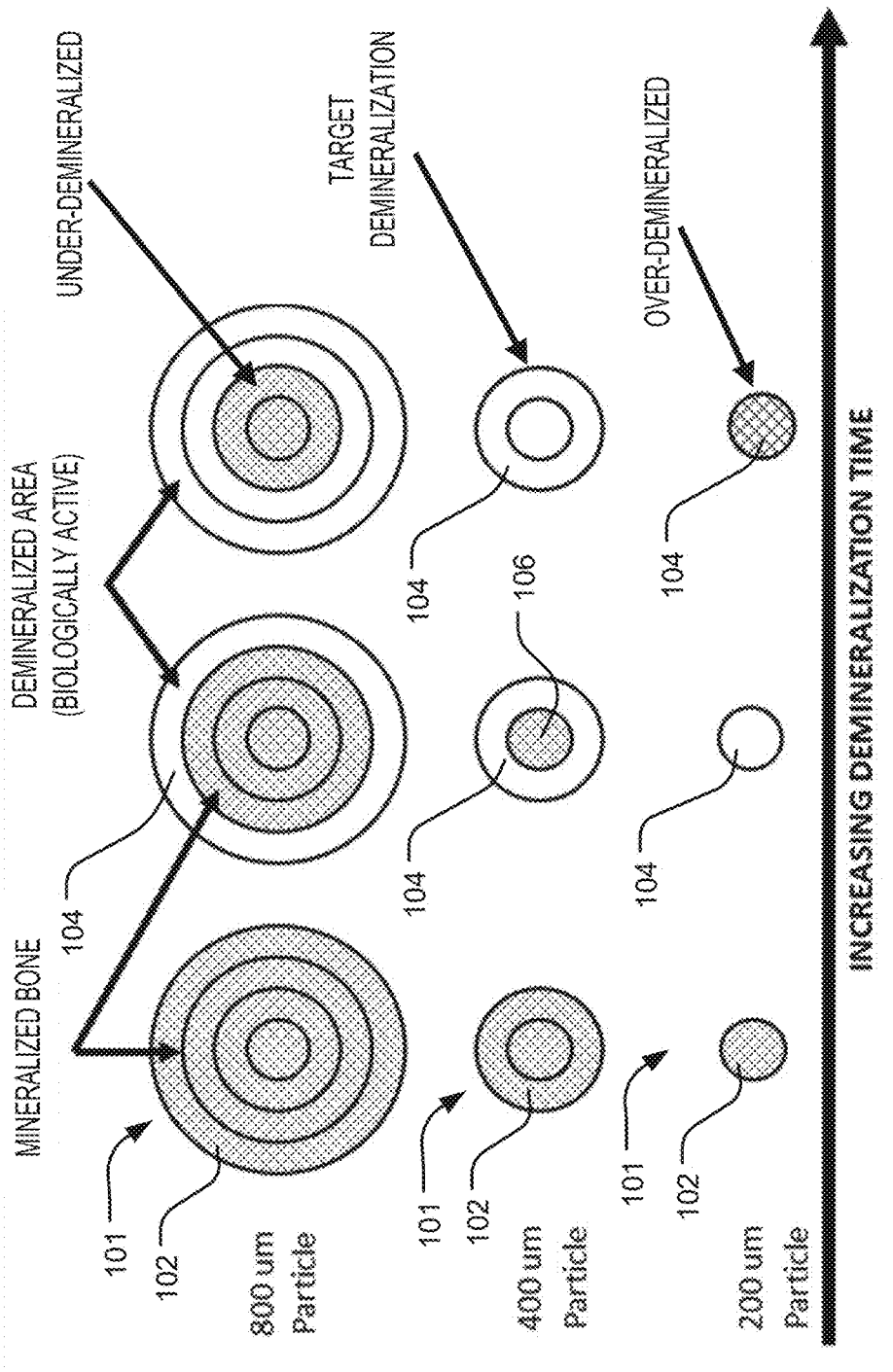
FIG. 1 shows an example of an "outside-in" progression of demineralization which can lead to over-demineralization.

For instance, as shown in the example scenario 100 depicted in FIG. 1, upon exposure of bone particles 101 to acid, the bone mineral 102 on the surface is dissolved, and a demineralization front 104 can be created. As demineralization progresses and bone mineral 102 is removed, the demineralization front 104 moves toward the center 106 of the particle 101 as acid reacts with the newly exposed bone mineral 102 deeper in the particle 101. As such, the "outside-in" demineralization process can be time dependent as it progresses from the surface towards the center 106 of the particle 101.

One issue with this process can be that smaller particles within the 125-850 μm size range can demineralize faster than larger particles due to their smaller particle diameter and increased surface area. Once the bone mineral is removed from a smaller particle, the acid begins to solubilize the desired growth factors into the acidic solution. When demineralization is complete, the acid solution, which contains growth factors, is discarded. The remaining DBM can contain growth factors, but the level can be decreased. Further, long acid exposure can denature the growth factor proteins still trapped in the collagen matrix. This combination of effects can lead to a reduction in the growth factor concentration in the resultant DBM particles and, consequently, a reduction in the osteoinductive potential/biological activity of these smaller DBM particles. Conversely, if the bone particles are at the upper size range, then the demineralization front 104 does not have enough time to reach the center of the bone particle, and a mineral core can be retained. Since the growth factors trapped in bone mineral would not be bioavailable, this can also reduce the osteoinductive potential of the DBM. Due to these issues, some demineralization processes have a limited range of particles that can be osteoinductive but also include smaller particles that can be over-demineralized (with growth factor loss/denaturing of OI proteins) and larger particles that can be partially demineralized (with reduced growth factor bioavailability). While products using this type of DBM can still be osteoinductive, the overall osteoinductivity and resulting biological activity can be decreased from its original potential.

Figure 2:
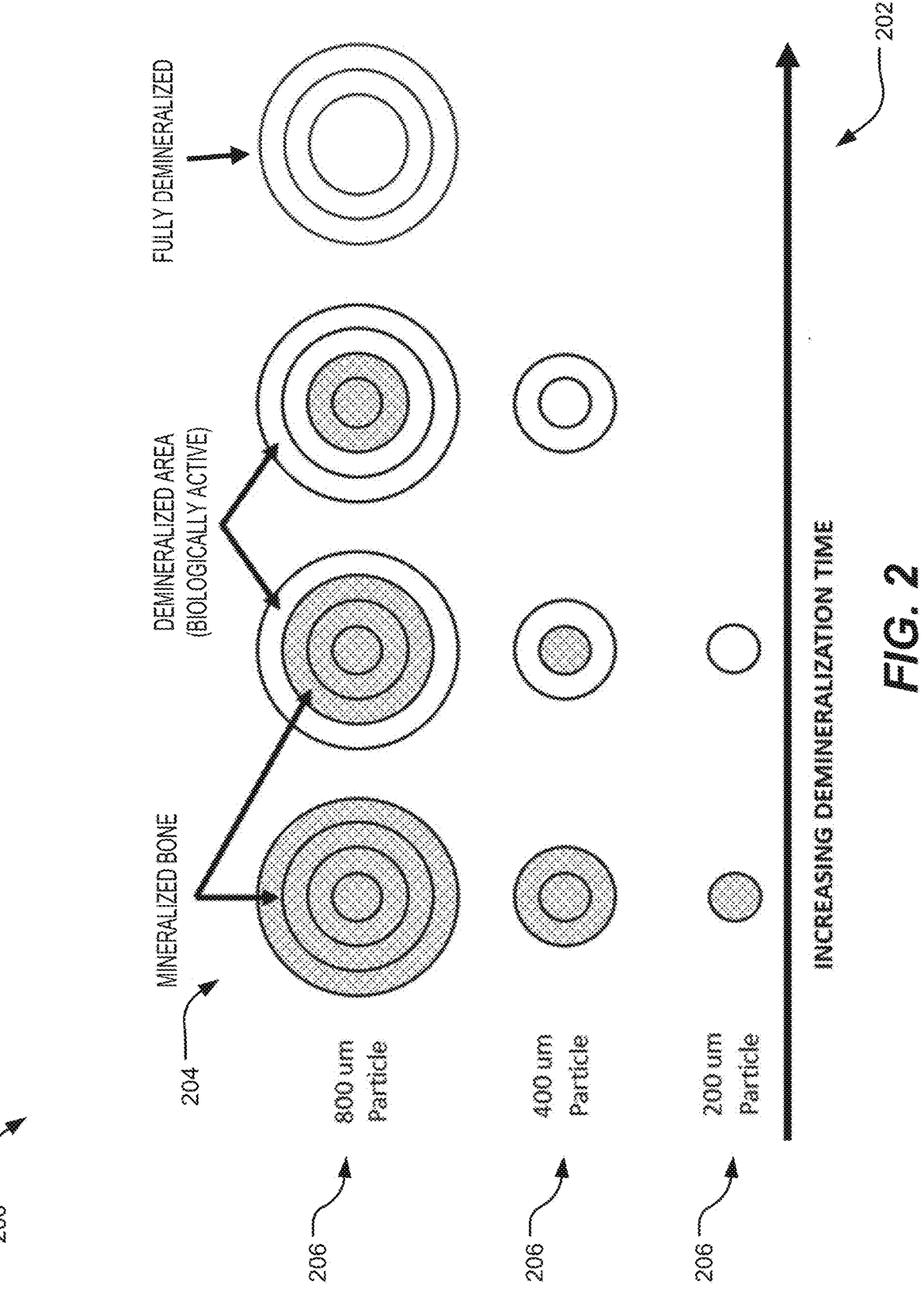
FIG. 2 shows an example size-optimized demineralization process where demineralization is stopped for different particle sizes prior to over-demineralization.

Turning to FIG. 2, the technology disclosed herein can address these limitations by using a system 200 with a sized-optimized demineralization process 202 to create biologically active and osteoinductive DBM throughout the entire particle size range. Additionally, the technology allows for the creation of small particle DBM (<125 μm) that can also be biologically active and osteoinductive.

Small particle DBM can have a number of advantages that have not been clinically utilized due to significant limitations with existing demineralization methods. These advantages include, but are not limited to, quick growth factor release that can be beneficial to bone formation; use in the creation of an osteoinductive coating on implantable devices; and the ability to augment other larger bone graft materials with an enhanced osteoinductive composition. These concepts have been unrealized due to the inability of previous demineralization processes to retain the biological activity (e.g., growth factor content) in small particles. This can be evident in various studies that have investigated the effect of DBM particle size on growth factor content and in vivo osteoinductivity. In these studies, various particles size ranges (e.g., including small particles <125 μm) were tested using the same broad particle size range demineralization process. Since the same broad size range particle process was used, the smaller particles demineralized at a much faster rate than larger particles and were subject to excessive demineralization. Testing of this small particle DBM showed a lack of osteoinductivity with little to no growth factors remaining. As such, these studies generally concluded that small particle DBM can be undesirable due to a lack of biological activity. Therefore, most DBM products do not contain particles that are <125 μm.

To address these issues, the compositions, systems 200, methods, and devices disclosed herein can provide an improved demineralization process by linking demineralization conditions (e.g., demineralization time, acid selection, and/or acid to bone ratio, etc.) to the particle size. This process can be called the "size-optimized demineralization 202" and can create enhanced DBM with higher growth factor content and an improved biological activity compared to other DBMs. Instead of a "one-size-fits-all" demineralization methodology, bone particles in the sized-optimized demineralization processes are separated into narrow size ranges and independently demineralized using process condition specific to each particle size. This can minimize over- and under-demineralization. The size-optimized demineralization process can effectively remove the bone mineral from the cortical bone but can retain a maximum amount of growth factors within the collagen matrix.

The technology disclosed herein also includes tissue repair compositions using the size-optimized DBM, compositions specific to previously unused small DBM particles, and protein isolation techniques to further enhance the size-optimized demineralization processes.

In some examples, a broad size range of DBM particles 204 can be demineralized by separating the cortical bone particles into multiple size range subsets 206 that use a narrow range (e.g., <150 µm). Each size range subset 206 can then be independently demineralized according to a custom process that can be optimized for each particle size range. This is shown in FIG. 2. By using this technique, the size-optimized demineralization process 202 can optimally remove the bone mineral while maintaining maximum growth factor levels. In some examples, the duration of the demineralization can be adjusted according to size. Since demineralization can be a time-based process as it progresses from the surface of the particle to the interior, the demineralization time can be optimally linked to particle size range. For example, the smallest size range can be demineralized using the shortest time. This can fully demineralize the particle without subjecting it to the prolonged demineralization needed for larger particles. With each increase in the size range, the demineralization time can be extended to allow for complete demineralization while preventing over-demineralization. Following the conclusion of demineralization for all the particles, the particles can be recombined into a single bulk amount and used in enhanced tissue repair compositions.

In some scenarios, an enhanced DBM can be purposely created from a small (e.g., <125 µm) cortical bone particle size range. For instance, small particle DBM (e.g., <125 µm) can be specifically targeted using the optimization processes discussed herein. While standard milling and grinding technique can create a 125-850 µm size range, a modified technique can be used to create particles <125 µm, as shown in FIG. 3.

Figure 3:
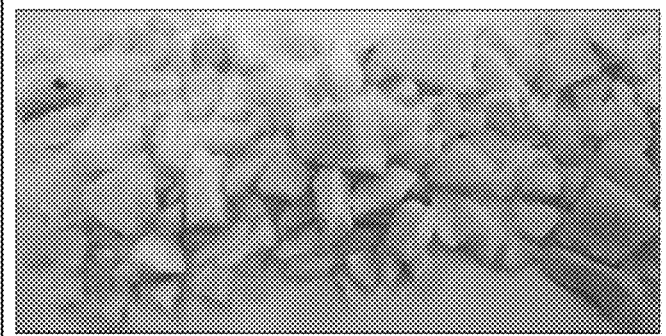
FIG. 3 shows an example small particle DBM generation method of using a cryomilling procedure.
Figure 3:
Figure 3:
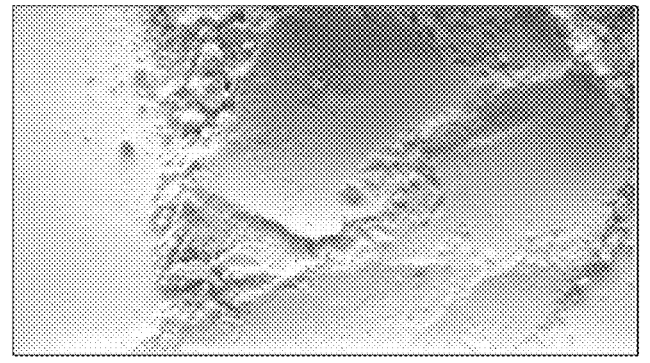

FIG. 3 depicts an example system 200 including a sized-optimized demineralization process 202 with a modified milling technique 302. The modified milling technique 302 can be used since certain milling techniques can have a propensity to generate heat during processing of small particles. This heat can negatively affect the DBM particles by denaturing and deactivating the growth factors. To compensate for this issue, cold temperature or cryogenic techniques can be employed for the modified milling technique 302 (e.g., "cryomilling"). This can be done by low temperature milling methods 304 that utilize liquid nitrogen, dry-ice, or freezers to lower the temperature of the particles during the milling process. In one example, a liquid nitrogen cryomill 306 can be used to reduce particle size to <125 µm without denaturing the growth factor proteins (e.g., as depicted FIG. 3). Once the small particle is obtained, the bone powder can be demineralized using a process optimized for small particles. For example, demineralization times can be adjusted due to the small particle size. With standard demineralization times ranging from 3-24 hours, demineralization of a small particle cortical bone powder can be adjusted to be <30 minutes. Other parameters such as type of acid, acid concentration, and/or acid-to-bone ratio can also be adjusted to create an optimal small particle demineralization process. Additionally, small particle demineralization can employ a multi-step process with an initial set of demineralization parameters and a second set of different parameters.

In another example of using the system 200 to create small particle DBM, particle size reduction can occur on the DBM, rather than the starting cortical bone. In this example, the size-optimized demineralization process 202 can be used on the standard 125-850 µm cortical bone particles. Once each size range is separately demineralized, the size optimized DBM particles can be recombined. The recombined DBM particles can then be subject to cryomilling techniques that can be used to further reduce the particle size to <125 µm.

In some scenarios, compositions, systems 200, and methods disclosed herein can include protein isolation from demineralization solutions.

For instance, another example of the technology disclosed herein can be used to address the issue with growth factors diffusion out of the DBM particles during demineralization (e.g., over-demineralization). Since demineralization solutions are typically discarded, any solubilized growth factors found in the solution are also discarded. This can reduce the growth factor concentration of the remaining DBM particles and lower its osteoinductivity and biological activity. In addition to the size-optimized demineralization process, protein isolation techniques can be used on the demineralization solutions. This includes, but is not limited to, using molecular weight filtration methods such as dialysis or diafiltration techniques to isolate the protein from the demineralization acid/solubilized bone mineral. Additionally, or alternatively, protein precipitation techniques using solutions such as ammonia sulfate, trichloroacetic acid, and/or acetone precipitation can be used. Further, protein isolation techniques can be used individually in or in combination with other techniques disclosed herein. Using these techniques, the growth factor solution can be recombined with the DBM particles to create an osteoinductive composition. In some examples, this can be done by freeze-drying the protein solution to create a protein powder that can then be mixed with the DBM particulate.

In some examples, the compositions, systems 200, and methods disclosed herein can include various osteoinductive compositions. For example, the disclosed technology can include using the enhanced DBM particles produced through a size-optimized demineralization process 202 in various tissue repair compositions. This can include using size-optimized DBM in various implant forms such as DBM powder or DBM fibers. The enhanced DBM can also be mixed with a moldable, bioabsorbable carrier to form DBM putties or gels, or with a fibrous material (e.g., collagen) to create a DBM sheet.

Further, the fine particle enhanced DBM powder (e.g., 1-50 µm sized powder) can be used as a coating for bone contacting implants and/or non-osteoinductive bone graft particles. This can be done by mixing the fine particle DBM with water or a water-based carrier and using it to coat other implants. For example, a porous ceramic bone graft can be made osteoinductive by dipping the ceramic in an aqueous dispersion of the small DBM powder to saturate the porosity with the suspended fine particle DBM. The aqueous dispersion can include water alone or use water with other soluble materials (e.g. gelatin, polymers, etc.) to aid in the coating process. The saturated particles can then be dried (e.g., via air drying or freeze-drying) to adhere the particles to the surface of the ceramic. The resulting bone graft can comprise an osteoinductive coating on the surface of the ceramic. In other applications, the coating can be applied to porous interbody fusion cages, porous coatings on joint replacement devices, and/or other porous implants that contact bone. Additionally, if the fine particle DBM is provided dry, a coating solution can be created in the operating room and applied to the implant during surgery.

Additionally, the fine particle DBM powder can be subjected to a secondary demineralization step to remove any remaining bone mineral, gently solubilize the growth factors and create collagen-based peptides (e.g. gelatin and/or hydrolyzed collagen). This growth factor peptide material can be isolated from the solution and used in various enhanced DBM formulations. The growth factor peptide can be used in a solution form or freeze-dried to create a dry form. In certain embodiments, due to the presence of bone-derived gelatin in the growth factor peptide, the rehydrated growth peptide solution can form a gel. In some applications, the growth factor peptide solution or gel can form an osteoinductive coating. In other applications, the growth factor peptide gel can be used as a carrier to create enhanced bone graft putties when combined with other particles, or fibers.

Additional advantages of the compositions, systems 200, methods, and devices discussed herein will become apparent from the additional examples discussed below.

Sized-Optimized Demineralization

The size-optimized demineralization processes 202 disclosed herein can result in DBM particles, fibers, or powders that can be specifically designed to maintain high growth factor content of the tissue, which can improve the osteoinductivity and biological activity of the resulting DBM. This enhanced DBM can then be used to create improved osteoinductive compositions for tissue repair. Although bone grafting applications can be a primary use of sized-optimized DBM, other musculoskeletal surgical applications are also envisioned. Additionally, while acid demineralization is described in some examples, other demineralization solutions or solutions that facilitate the demineralization process may also be used. For these non-acid solutions, the same demineralization process control parameters apply, such as solution concentration, demineralization time, ratio of solution-to-bone, and so forth.

Some example systems 200 can include enhanced DBM created from a broad cortical bone particle size range. As used herein, the term "size range" refers to a range of absolute particle sizes. For example, a size range of 100 μm to 150 μm encompasses particles having a size between 100 μm and 150 μm (i.e., 101 μm, 102 μm, 103 μm, 104 μm, 105 μm, 106 μm, 107 μm, 108 μm, 109 μm, 110 μm, 111 μm, 112 μm, 113 μm, 114 μm, 115 μm, 116 μm, 117 μm, 118 μm, 119 μm, 120 μm, 121 μm, 122 μm, 123 μm, 124 μm, 125 μm, 126 μm, 127 μm, 128 μm, 129 μm, 130 μm, 131 μm, 132 μm, 133 μm, 134 μm, 135 μm, 136 μm, 137 μm, 138 μm, 139 μm, 140 μm, 141 μm, 142 μm, 143 μm, 144 μm, 145 μm, 146 μm, 147 μm, 148 μm, 149 μm, 150 μm, and any intermediate sizes thereof). As another example, a size range of <100 μm encompasses particles with a size less than 100 μm (i.e., <<100 μm, <99 μm, <98 μm, <97 μm, <96 μm, <95 μm, <94 μm, <93 μm, <92 μm, <91 μm, <90 μm, <89 μm, <88 μm, <87 μm, <86 μm, <85 μm, <84 μm, <83 μm, <82 μm, <81 μm, <80 μm, <79 μm, <78 μm, <77 μm, <76 μm, <75 μm, <74 μm, <73 μm, <72 μm, <71 μm, <70 μm, <69 μm, <68 μm, <67 μm, <66 μm, <65 μm, <64 μm, <63 μm, <62 μm, <61 μm, <60 μm, <59 μm, <58 μm, <57 μm, <56 μm, <55 μm, <54 μm, <53 μm, <52 μm, <51 μm, <50 μm, <49 μm, <48 μm, <47 μm, <46 μm, <45 μm, <44 μm, <43 μm, <42 μm, <41 μm, <40 μm, <39 μm, <38 μm, <37 μm, <36 μm, <35 μm, <34 μm, <33 μm, <32 μm, <31 μm, <30 μm, <29

μm, <28 μm, <27 μm, <26 μm, <25 μm, <24 μm, <23 μm, <22 μm, <21 μm, <20 μm, <19 μm, <18 μm, <17 μm, <16 μm, <15 μm, <14 μm, <13 μm, <12 μm, <11 μm, <10 μm, <9 μm, <8 μm, <7 μm, <6 μm, <5 μm, <4 μm, <3 μm, <2 μm, or <1 μm).

For instance, a size-optimized demineralization process 202 for a broad size range of cortical bone particles can be envisioned. The starting point for a size-optimized demineralization process 202 can be the separation of bone into relatively narrow particle size ranges. Sieving can be one method of particle separation, but other techniques known in the art can also be used. Some sieve sizes can include one or more of the following sieve openings: 2 μm, 10 μm, 20 μm, 25 μm, 32 μm, 38 μm, 45 μm, 53 μm, 63 μm, 75 μm, 90 μm, 106 μm, 125 μm, 150 μm, 180 μm, 212 μm, 250 μm, 300 μm, 355 μm, 425 μm, 500 μm, 600 μm, 710 μm, 850 μm, 1.0 mm, or larger. Additionally, or alternatively, custom sieves with other sieve openings can be used. During processing, sieving can be conducted by a variety of techniques including manual shaking, mechanical shaking, and/or ultrasonic shaking. Ultrasonic shaking can be used for small particles (e.g., <250 μm). Particle separation processes can involve a single technique or multiple techniques, such as sequential sieving through mechanical shaking and then ultrasonic shaking. Additionally, griding mills can be fit with sieve screens to purposely generate desired size ranges.

In some examples, an advantage of the size-optimized demineralization process 202 can be that the demineralization process can be modified based on particle size. This can be done by using narrow particle ranges (e.g., <400 μm, <200 μm, or <150 μm). The use of narrow size ranges can minimize over- and under-demineralization.

Additionally, the size-optimized demineralization process 202 can provide the creation of fine particle DBM (e.g., <125 μm) that has previously been considered to be inactive. The addition of this size range can expand the size range of earlier DBMs (e.g., typically in the range of 125-850 μm) to include particles less than 125 μm in size, which would advantageously increase the DBM yield from the donor bone. The fine particle DBM (<125 μm) can also be purposely created to form osteoinductive coatings or an optimal starting material for a growth factor peptide process.

In one example, the size range sub-sets can be chosen such that the overall range between the sub-sets is relatively similar. The following size range sub-sets, based on sieve sizes, can be used to separate the starting cortical bone: less than 90 μm, 90 μm to less than 212 μm, 212 μm to less than 355 μm, 355 μm to less than 500 μm, 500 μm to less than 600 μm, 600 μm to less than 710 μm, and/or 710 μm to less than 850 μm. As shown in Table 1, the overall range in each sub-set is relatively uniform and spans 90 μm to 145 μm. The uniformity of these size ranges, aids in the consistency of the demineralization process. With seven groups of particles, the demineralization process can be modified to each size range to create seven independent demineralization processes. It is to be understood that other numbers of particle size groups can be used (e.g., two, three, four, five, six, eight, nine, ten, etc.). In one example, demineralization times for the different size ranges can be changed while the other demineralization parameters can be left constant. Since smaller particles demineralize faster, shorter demineralization times can be employed. Matching a demineralization time to particle size can be optimized by analyzing residual calcium levels and/or growth factor content of the resultant DBM particles. Various residual calcium levels can be targeted <8%, <4%, or <2%.

11

TABLE 1

| Size Range Sub-Set (based on standard sieves) | Overall Range | Example Demineralization Time |
|---|---|---|
| <90 μm | 90 μm | 15 minutes |
| 90-212 μm | 122 μm | 23 minutes |
| 212-355 μm | 143 μm | 34 minutes |
| 355-500 μm | 145 μm | 50 minutes |
| 500-600 μm | 100 μm | 75 minutes |
| 600-710 μm | 110 μm | 113 minutes |
| 710-850 μm | 140 μm | 170 minutes |

Additionally, the demineralization process for the various size ranges can be customized by a type of acid and/or acid concentration.

In some aspects, different types of acids can be used to demineralize particles of different size ranges. In some aspects, larger particle sizes can be demineralized using a strong acid (e.g., a stronger type of acid than used to demineralize smaller particles). In other aspects, smaller particle sizes can be demineralized using a weak acid. Weak and strong acids are identified chemically by their propensity to dissociate in aqueous solution. Weak acids only partially dissociate, and strong acids fully dissociate. This corresponds to the dissociation constant (Ka) of the acid, which represents the equilibrium constant for the dissociation reaction of the acid in aqueous solution when the acid donates a proton (H+) to water to form its conjugate base (A−) and a hydronium ion (H3O+). Weak acids are characterized by a pK in a range of about −2 to 12. Strong acids are characterized by a pK of around −2. In general, a stronger type of acid can have a lower pK than a weaker acid. Conversely, a weaker type of acid can have a higher pk than a stronger type of acid. Exemplary weak acids include, but are not limited to, citric acid (C6H8O7), acetic acid (CH3COOH), oxalic acid (HO2C2O2H), sulfurous acid (H2SO3), hydrogen sulfate ion (HSO4-), phosphoric acid (H3PO4, Pitrous acid (HNO2), hydrofluoric acid (HF), methanoic acid (HCO2H), benzoic acid (C6H5COOH), and formic acid (HCOOH). Exemplary strong acids include, but are not limited to, hydrogen chloride (HCl), nitric acid (HNO3), hydroiodic acid (HI), perchloric acid (HClO4), and chloric acid (HClO3).

In some aspects, different concentrations of acids can be used to demineralize particles of different size ranges. In some aspects, larger particle sizes can be demineralized using a high concentration of an acid (e.g., a strong or weak acid). In other aspects, smaller particle sizes can be demineralized using a low concentration of an acid (e.g., a strong or weak acid). As used herein, the concentration of the acid (low to high concentration) can span 0.01 M to about 4 M. For example, a high concentration of an acid (e.g., a strong or weak acid defined above) can be from about 0.5 M to 4 M (e.g., 0.5 M, 1.0 M, 1.5 M, 2.0 M, 2.5 M, 3.0 M, 3.5 M, 4.0 M). In other aspects, a low concentration of an acid (e.g., a strong or weak acid defined above) can be from about 0.01 M to about 0.1 N (e.g., 0.01 M, 0.2 M, 0.3 M, 0.4 M, 0.05 M, 0.06 M, 0.07 M, 0.08 M, 0.09 M, or 0.1 M).

In some aspects, therefore, a strong acid (e.g., HCl) can be used at a concentration of about 0.5M to demineralize larger particle sizes. In some instances, 0.5 M hydrochloric acid (equivalent to 0.5 N) can be a primary demineralization solution used in demineralization processes. At the same time, a weak acid (e.g., 3 M citric acid) can be used to demineralize smaller particle sizes. Alternatively, a strong acid (e.g., HCl) can be used at a low concentration of about 0.1 N, 0.5 N, or 0.01 N can be used to demineralize smaller particles.

Alternatively, if desired for manufacturing purposes, the total demineralization time can be held uniform, while custom demineralization solutions can be utilized for the different size ranges. Further, two-step demineralization methods may be used where stronger acids (such as 0.5 M HCl) can be used to remove a portion of the bone mineral and a secondary demineralization with a weak acid (e.g. 3 M citric acid) can be used to gently remove the remaining bone mineral or to create soluble growth factor peptides. As a general guidance, demineralization parameters (e.g., such as demineralization time, acid selection, acid to bone ratio, and/or acid concentration) can be optimized to effectively remove the bone mineral while minimizing diffusion/degradation of growth factor proteins (over-demineralization). Following demineralization, the DBM can be processed using various techniques (e.g., neutralization, rinsing, freeze drying, etc.).

In some examples, the composition(s) and method(s) of the system(s) 200 disclosed herein can include enhanced DBM specifically created from a small cortical bone particle size range (<125 μm).

Unlike other demineralization methods, one advantage of a size-optimized demineralization process 202 can be that fine particle DBM (e.g., <125 μm) can be processed to retain its growth factor content and biological activity. In other demineralization processes and compositions, this size range was not used due to its low growth factor content that was the result of over-demineralization. In the sized-optimized demineralization process, small particle DBM with retained growth factor content and biological activity can be created. In one example, this can be done by milling the starting cortical bone using techniques that minimize heat generation during milling. For example, cryomilling can create cortical bone particles <50 μm. This is shown in FIG. 3. In this example, bovine cortical bone was used. The bone was initially milled to a <8 mm particle size. The milled bone was then placed in a liquid nitrogen cryomill to reduce the size further. By adjusting the cryomilling time, various particle size ranges can be created.

Figure 4:
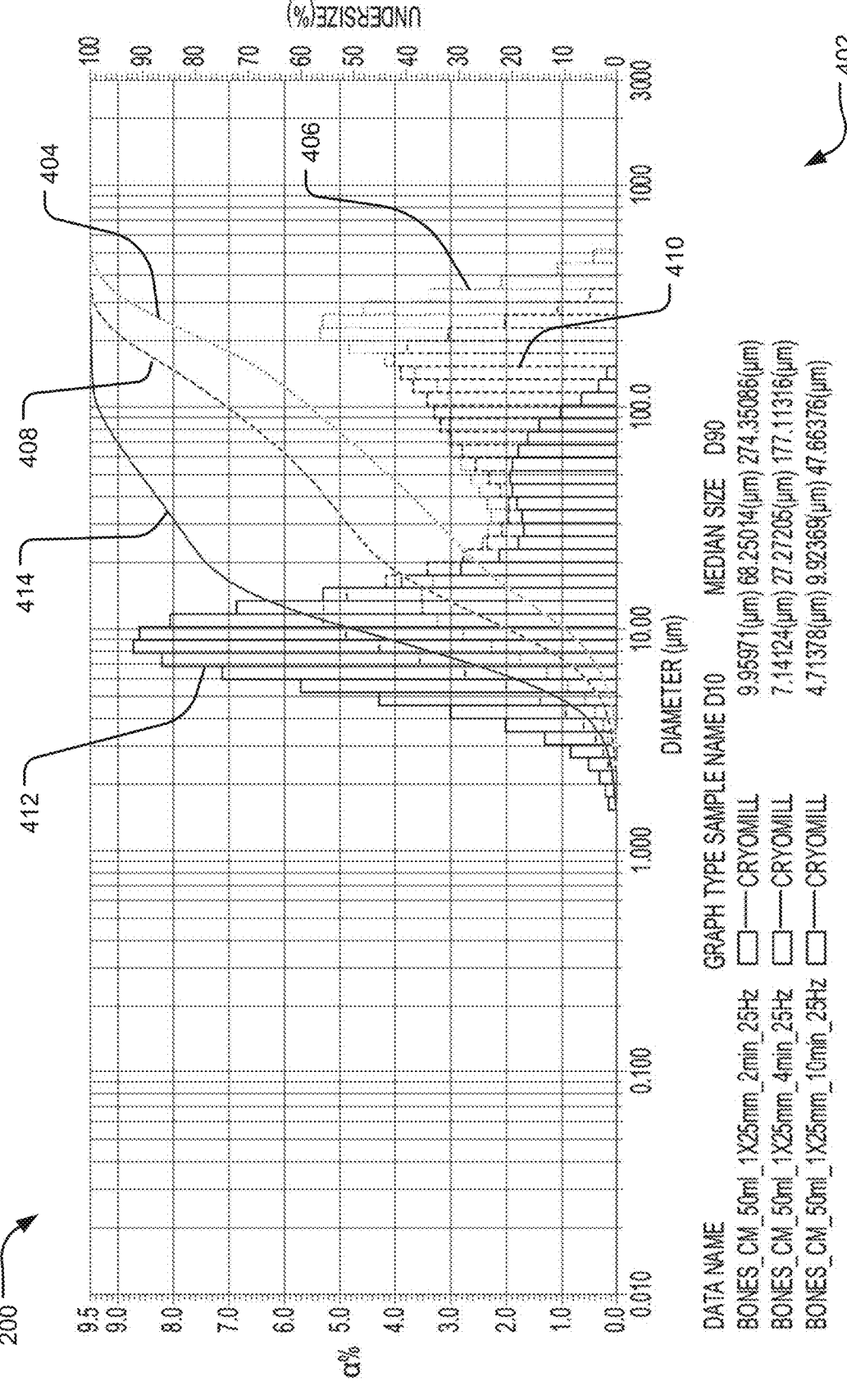
FIG. 4 shows increased cryomilling time to reduce particle size.

Turning to FIG. 4, a particle size analysis 402 of bone cryomilled for various times can show a reduction in size with increased cryomilling time. In this example system 200, the following average size ranges can be obtained: 68 μm (e.g., after 2 minutes of cryomilling, shown as dotted line 404 and dotted bars 406), 27 μm (e.g., after 4 minutes of cryomilling, shown as dashed line 408 and dashed bars 410), and/or 10 μm (e.g., after 10 minutes of cryomilling, shown as solid line 412 and solid bars 414).

Using cryomilling or other small particle grinding techniques, the system 200 can further mill standard cortical bone powder (e.g., 125-850 μm) to produce a fine powder with particles having size range sub-sets such as <25 μm, <50 μm, <53 μm, <75 μm, <90 μm, <125 μm. Once the fine particle cortical bone is formed and sieved, it can be subjected to a demineralization process that can be modified to be faster than standard demineralization times in order to minimize over-demineralization.

Due to these fast demineralization times, weaker acids and/or lower acid concentrations may be used to prolong the demineralization time in order to make the process less time sensitive. Following demineralization, the DBM can be further processed using various techniques (e.g., neutralization, rinsing, freeze drying). The use of a filter or centrifuge can provide additionally improved control and yield by separating the fine particle DBM powder from the processing solutions.

Growth Factor Peptide Material

Figure 7:
FIG. 7 shows growth factor peptide after freeze drying.

Additionally, or alternatively, the fine particle DBM powder (e.g., <125 μm) can be subject to further processing (e.g. secondary demineralization) to gently hydrolyze the collagen matrix and create a growth factor peptide material that comprises soluble growth factor proteins and soluble collagen (e.g. gelatin and/or hydrolyzed collagen). In a growth factor peptide process, the growth factor content of the end material is only as good as the growth factor content of the starting DBM. Therefore, the fine particle DBM powder can be unique and advantageous as a starting material to this growth factor peptide process due to the higher growth factor content of the size-optimized fine particle DBM powder. Additionally, the use of fine particle DBM in a growth factor peptide process results in higher yields due to the higher surface area of the fine particles, which increases acid exposure. This combination of factors can result in growth factor peptide material with higher growth factor content and higher yields, which is advantageous over the use of broadly sized DBM particles in a growth factor peptide process. Accordingly, provided herein are growth factor peptide solutions and powders prepared by the methods herein. Following the generation of a growth factor peptide solution, the growth factor peptide can be further processed using protein isolation techniques to remove residual processing chemicals (e.g., acids, salts, etc.). The isolated growth factor peptide solution can then be freeze dried. Once freeze-dried, the growth factor peptide can be in a foam, powder, or "cotton-like" material (e.g., as shown in FIG. 7). The resulting freeze-dried growth factor peptide can be combined with other allograft bone forms from the same tissue donor or kept in a growth factor peptide form.

An advantage of the growth factor peptide can be that, when it is resolubilized with water at certain concentrations, an osteoinductive gel can be formed. This gel can function as a carrier for other bone graft particles or fibers which can result moldable bone graft putties and/or injectable/flowable bone graft gels. An additional advantage is that the growth factor peptide can bind various materials together to form a rigid osteoinductive implant that can be inserted into other musculoskeletal implants. For example, the growth factor peptide can be mixed with size optimized DBM, cortical bone particles, and/or cancellous bone particles to form an osteoinductive composition. This composition can be molded into a shape and size that is matched to a musculoskeletal implant, including interbody fusion cages, interspinous spacers, pedicle screws, sacroiliac screws, fracture screws, intermedullary nails, Cotton and Evans wedges, tibial plateau fracture wedges, and others. Following freeze-drying, the osteoinductive composition can retain the molded form and have a rigid consistency. This allows the osteoinductive form to be inserted into the musculoskeletal implant at the time of surgery. This is particularly advantageous for implants with narrow cavities (e.g. cannulated screws) that could not be filled by other bone graft putties or gels.

In some examples, the composition(s) and method(s) of the system(s) 200 disclosed herein can include protein isolation from demineralization solutions.

For example, in some demineralization processes, the demineralization solution is discarded following demineralization. If a particle becomes over-demineralized, growth factors can diffuse out the collagen matrix into the demineralization solution. This can reduce the growth factor content of the DBM and reduce its biological activity. To further minimize growth factor loss during demineralization, protein isolation techniques disclosed herein can be used on the demineralization solutions from the sized-optimized process. In one example, acid demineralization solutions with solubilized bone mineral can be neutralized with a base (e.g., sodium hydroxide-NaOH). The addition of a base can precipitate the solubilized bone mineral in a salt form. The bone mineral can then be removed from the remaining solution using various techniques such as decanting and/or centrifugation. Additionally, or alternatively, the acid demineralization solution can be subjected to dialysis or diafiltration with a low molecular weight cutoff membrane (e.g., 5 k Da). The use of this molecular weight cut-off can purposely retain growth factor proteins with a molecular weight >5 k Da, while allowing other ions, salts, and solutes to diffuse out. The resulting isolated growth factor protein solution can be freeze-dried and/or recombined with the enhanced DBM.

Osteoinductive Compositions

In some instances, the composition(s) and method(s) disclosed herein can include various osteoinductive compositions.

For example, by using the disclosed size-optimized demineralization process 202, a variety of enhanced demineralized bone matrix (DBM) compositions can be produced. Particles in a standard size range (e.g., 125-850 μm) can be demineralized by size to create enhanced DBM compositions with a higher growth factor content and more biological activity than other DBMs.

In various aspects, an enhanced demineralized bone matrix (DBM) composition is provided comprising osteoinductive demineralized bone matrix (DBM) particles wherein the osteoinductive DBM bone particles comprise at least two different size ranges, wherein the first size range comprises a larger particle size than the second size range. In various aspects, the first size range is selected from the group consisting of <90 μm, <125 μm, 90 μm to less than 212 μm, 212 μm to less than 355 μm, 355 μm to less than 500 μm, 500 μm to less than 600 μm, 600 μm to less than 710 μm, and 710 μm to less than 850 μm; and the second size range is selected from the group consisting of <90 μm, <125 μm, 90 μm to less than 212 μm, 212 μm to less than 355 μm, 355 μm to less than 500 μm, 500 μm to less than 600 μm, 600 μm to less than 710 μm, and 710 μm to less than 850 μm. In some aspects, the at least two different size ranges comprise at least one of <125 μm, <90 μm, <75 μm, <53 μm, <50 μm, or <25 μm. In some aspects, the at least two different size ranges comprise at least one of <125 μm, <90 μm, or <53 μm. In some aspects, the at least two different size ranges comprise at least one of <125 μm.

In some aspects, an enhanced DBM composition is provided comprising two or more sizes of particles. For example, the enhanced DBM composition may comprise a first set of particles having an average size of <90 μm, <125 μm, 90 μm to less than 212 μm, 212 μm to less than 355 μm, 355 μm to less than 500 μm, 500 μm to less than 600 μm, 600 μm to less than 710 μm, and 710 μm to less than 850 μm and a second set of particles having an average size of <90 μm, <125 μm, 90 μm to less than 212 μm, 212 μm to less than 355 μm, 355 μm to less than 500 μm, 500 μm to less than 600 μm, 600 μm to less than 710 μm, and 710 μm to less than 850 μm.

In some aspects, an enhanced DBM composition is provided comprising three or more sizes of particles. For example, the enhanced DBM composition may comprise a first set of particles having an average size of <90 μm, <125 μm, 90 μm to less than 212 μm, 212 μm to less than 355 μm, 355 μm to less than 500 μm, 500 μm to less than 600 μm, 600 μm to less than 710 μm, and 710 μm to less than 850 μm, a second set of particles having an average size of <90 μm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, and a third set of particles having an average size <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm.

In some aspects, an enhanced DBM composition is provided comprising four or more sizes of particles. For example, the enhanced DBM composition may comprise a first set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a second set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a third set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, and a fourth set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm.

In some aspects, an enhanced DBM composition is provided comprising five or more sizes of particles. For example, the enhanced DBM composition may comprise a first set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a second set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a third set of particles having an average size <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a fourth set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, and a fifth set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm.

In some aspects, an enhanced DBM composition is provided comprising six or more sizes of particles. For example, the enhanced DBM composition may comprise a first set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a second set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a third set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a fourth set of particles having an average size <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, a fifth set of particles having an average size <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm, and a sixth set of particles having an average size of <90 µm, <125 µm, 90 µm to less than 212 µm, 212 µm to less than 355 µm, 355 µm to less than 500 µm, 500 µm to less than 600 µm, 600 µm to less than 710 µm, and 710 µm to less than 850 µm.

In some aspects, the enhanced DBM composition may comprise particles having an average size of <25 µm, <50 µm, <53 µm, <75 µm, <90 µm, or <125 µm. In some aspects, the enhanced DBM composition may comprise particles having an average size of <25 µm. In some aspects, the enhanced DBM composition may comprise particles having an average size of <50 µm. In some aspects, the enhanced DBM composition may comprise particles having an average size of <53 µm. In some aspects, the enhanced DBM composition may comprise particles having an average size of <75 µm. In some aspects, the enhanced DBM composition may comprise particles having an average size of <90 µm. In some aspects, the enhanced DBM composition may comprise particles having an average size of <125 µm.

These enhanced DBM particles can be used "as-is" as a tissue repair composition (e.g., enhanced DBM Powder). Additionally, or alternatively, the enhanced DBM particles can be combined with a biocompatible carrier to form various tissue repair compositions. The biocompatible carrier can include, but is not limited to, polymers/copolymers (e.g., Pluronic/Poloxamer family of compounds), phospholipids (e.g., lecithin, triglyceride oils), carboxymethylcellulose, hyaluronic acid, alginate, glycerol, and/or collagen fibers. Carriers can be selected to create enhanced DBM products (e.g., tissue repair compositions) in a variety of forms (e.g., putties, gels, and sheets).

Additionally, the ability of the size-optimized demineralization process 202 to create biologically active DBM powder with a small size range (e.g., <125 µm) can create a new application as an osteoinductive coating (e.g., an "OI coating"). OI coating can be based on fine particle DBM and/or the growth factor peptide. OI coatings can be beneficial for adding biological activity to scaffolds and/or implants that are osteoconductive (e.g., support bone formation on the surface of the material). For example, an OI coating can be used on a variety of musculoskeletal products that interface with bone and/or can be designed to promote bone growth into the implant. This can include porous implants such as bone graft materials, interbody fusion cages used in spine surgery, and/or joint replacement implants with porous surfaces.

In some examples, the OI coating based on fine particle DBM can occur during manufacturing. In one example, the fine particle DBM can be suspended in an aqueous solution to aid in the coating process. A slurry can be created by suspending the fine particle DBM in water or a slightly viscous carrier that can adhere to the surface of the implant. The carrier for the slurry can be selected from a variety of biocompatible, resorbable carriers. The carrier can be an aqueous material that can adhere and can be dried on the surface of the scaffold/implant. This can include hydrogels formed from natural materials such as gelatin, collagen, sodium hyaluronate, alginate, fibrin, chondroitin sulfate, agar/agarose, and/or combinations thereof. This can also include hydrogels formed from synthetic materials such as poly(ethylene glycol), poly (ethylene oxide), poly (propylene oxide), poly vinyl alcohol, and/or combinations thereof.

Any of these materials may be combined or used alone. In selecting the carrier and/or carrier solution concentration, the slurry can be flowable enough to penetrate the pore structure. This can be controlled by adjusting the concentration and resultant viscosity of the slurry.

In another example, fine particle DBM can be converted into a growth factor peptide, growth factor peptide solution and/or growth factor peptide powder as described herein. In a solution or gel form, the growth factor peptide, growth factor peptide solution and/or growth factor peptide powder can also be adhered or dried on the surface of a scaffold/implant as an OI coating. The ratio of growth factor peptide, growth factor peptide solution and/or growth factor peptide powder to water can be used to control the growth factor content of the OI coating.

In some scenarios, once the OI coating is formed, it can be applied to a bone graft scaffold or musculoskeletal implant. This can be done by immersing the scaffold/implant in the liquid OI coating such that the OI coating adheres to the surface. For porous or irregular surfaces, the slurry can be agitated using sonication or mixing methods to ensure complete coating and/or penetration into the porosity of the implant. Additionally, or alternatively, vacuum impregnation techniques can be used to ensure complete penetration of the liquid coating into the porosity. Once the coating is applied, it can be dried onto the surface. This can be done by air-drying, freeze-drying, and/or other drying techniques. The coating process can be created from a single immersion/drying step or can be created from multiple immersion/drying steps. Following the coating process, the resulting scaffold/implant can have a layer of dried OI coating on its surface. If a carrier is used, upon implantation, the carrier can hydrate and be quickly absorbed. The OI powder can also hydrate and begin releasing OI proteins.

In another example, the fine particle DBM or growth factor peptide, can be provided in a dry form designed to be rehydrated during surgery. This form can comprise fine particle DBM, fine particle DBM mixed with freeze-dried proteins isolated from the demineralization solution and/or a freeze-dried growth factor peptide. In this application, the material can be mixed in the operating room with blood, bone marrow aspirate, sterile saline, and/or other sterile liquids. The resultant combination can be used to coat other bone contacting implants and/or mixed with other bone graft materials to provide a source of osteoinductive growth factors.

Figure 5:
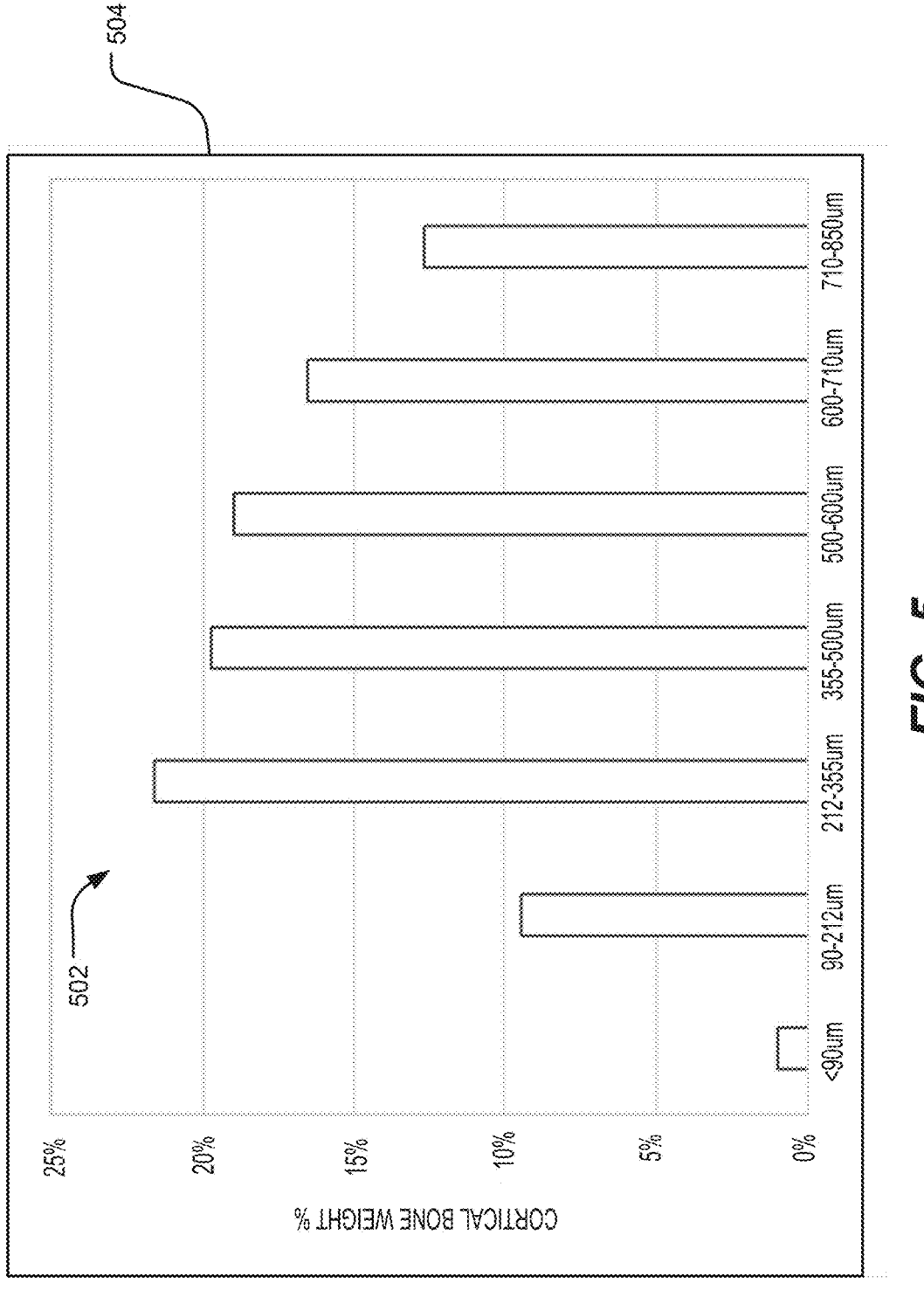
FIG. 5 shows the size distribution of milled cortical bone following sieving.

FIG. 5 shows an example system 200 having a size distribution 502 of milled cortical bone following sieving (e.g., as represented by a bar graph 504). As shown in FIG. 5, a first size subset of <90 μm particles can comprise 0.5%-2% of the composition; a second size subset of 90-212 μm particles can comprise 8%-10% of the composition; a third size subset of 212-355 μm particles can comprise 21%-23% of the composition; a fourth size subset of 355-500 μm particles can comprise 18%-20% of the composition; a fifth size subset of 500-600 μm particles can comprise 17%-19% of the composition; a sixth size subset of 600-710 μm particles can comprise 16%-18% of the composition; and/or a seventh size subset of 710-850 μm particles can comprise 12%-14% of the composition. The system 200 depicted in FIG. 5 can be similar to and/or can form at least a portion of any of the system(s) 200 disclosed herein.

Figure 6:
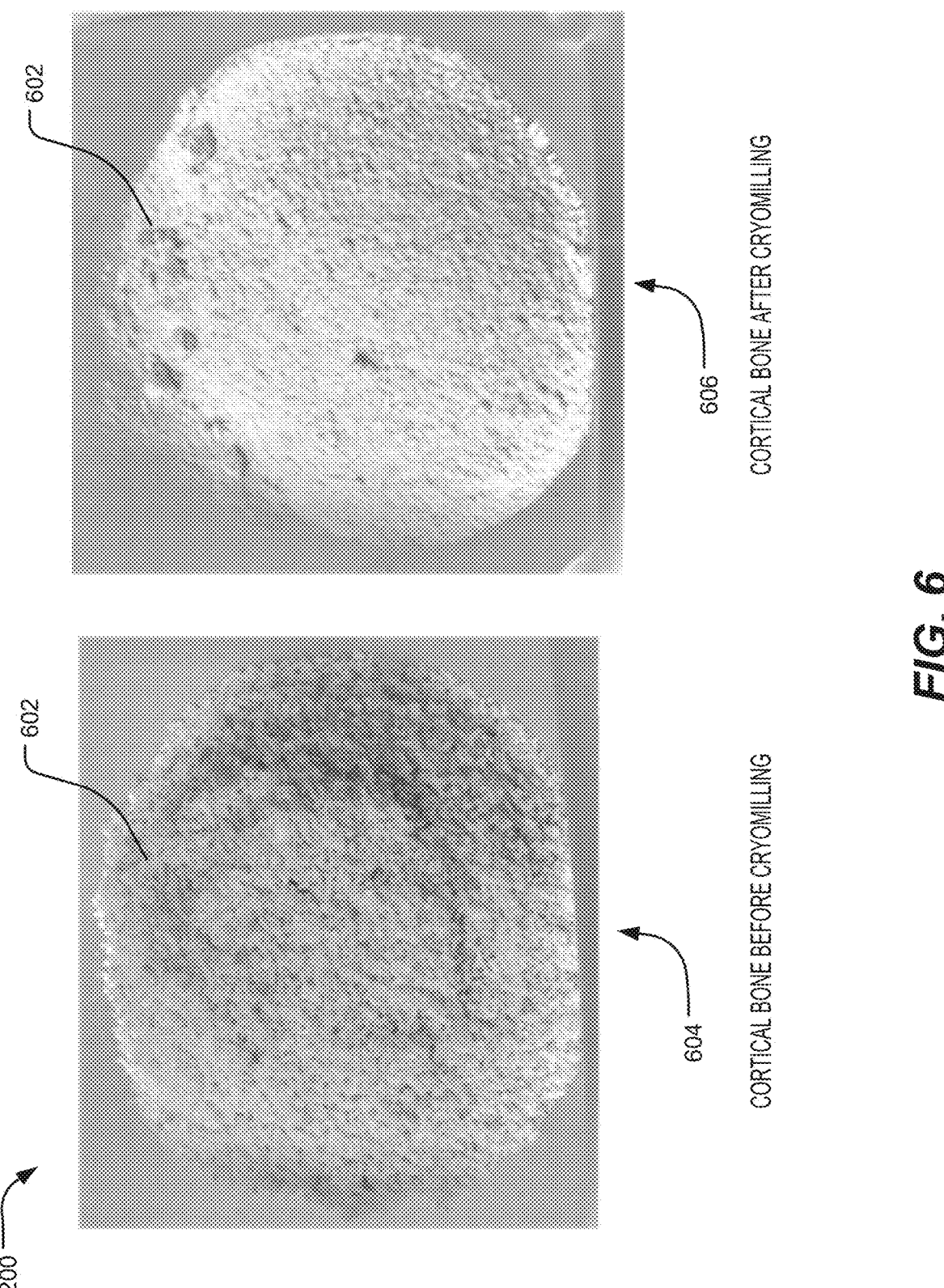
FIG. 6 shows cortical bone powder before and after cryomilling.

FIG. 6 shows an example system 200 including cortical bone powder 602 before milling 604 and after cryomilling 606. The system 200 depicted in FIG. 6 can be similar to and/or can form at least a portion of any of the system(s) 200 disclosed herein.

FIG. 7 shows an example system 200 including a growth factor peptide 702 after freeze drying. As shown in FIG. 7, the growth factor peptide 702 can have a "cotton-like" appearance, texture, and/or form-factor. The system 200 depicted in FIG. 7 can be similar to and/or can form at least a portion of any of the system(s) 200 disclosed herein.

Figure 8A:
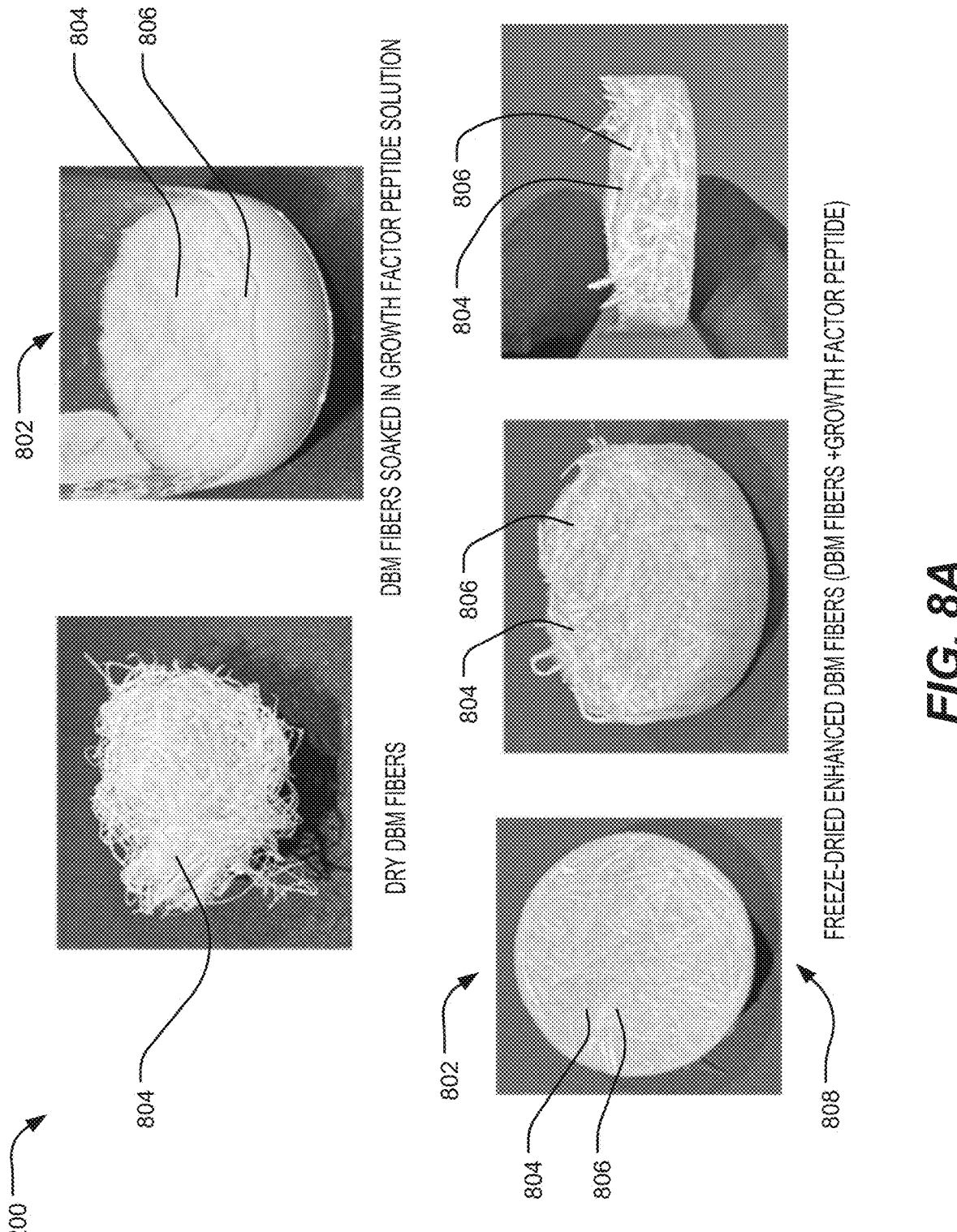
FIGS. 8A and 8B show an enhanced osteoinductive composition comprising DBM fibers coated with growth factor peptide.
Figure 8B:
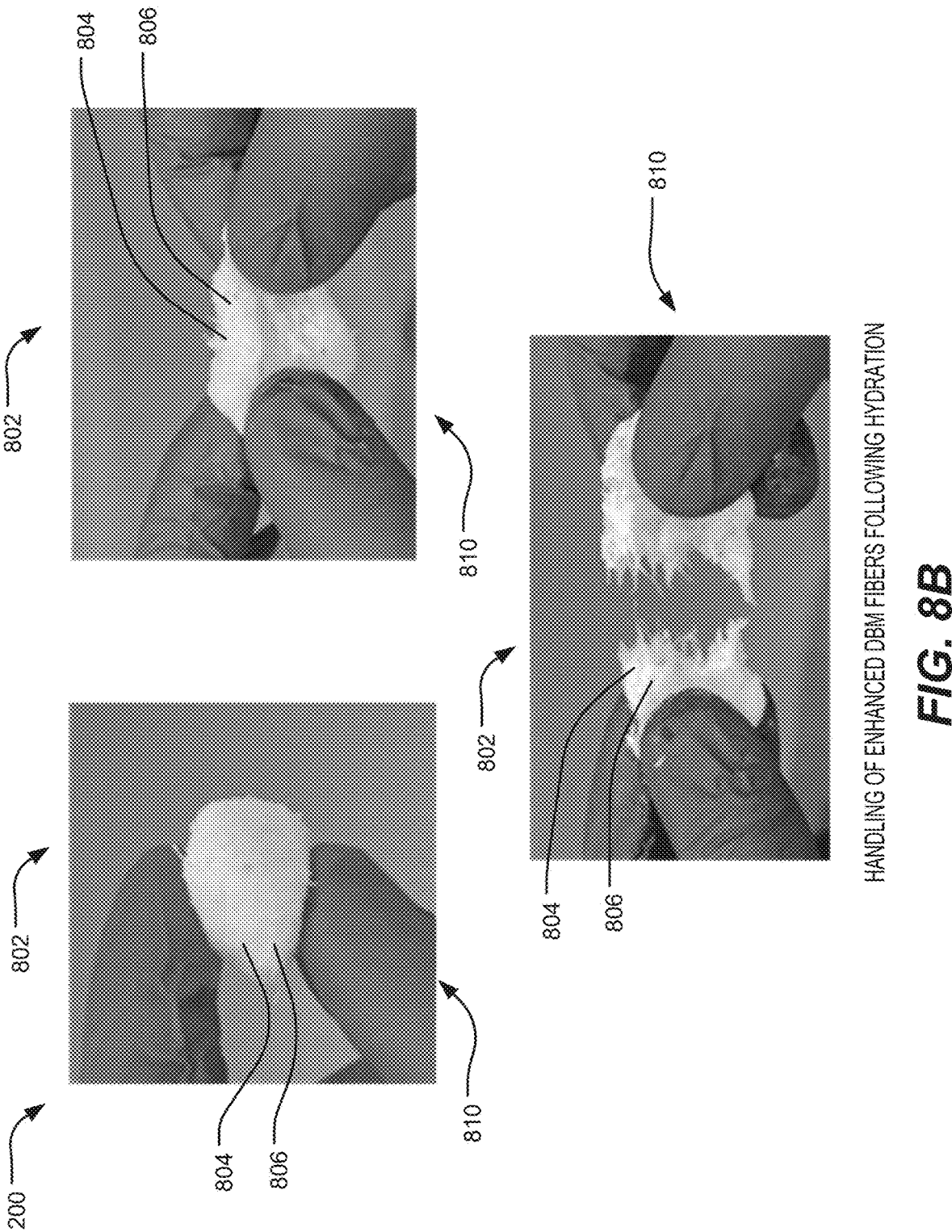

FIGS. 8A and 8B shows an example system 200 including an enhanced osteoinductive composition 802 comprising DBM fibers 804 coated with growth factor peptide 806. As shown, in FIG. 8A, the enhanced osteoinductive composition 802 can undergo a freeze-drying procedure to form a freeze-dried enhanced osteoinductive composition 808. As shown in FIG. 8B, the freeze-dried enhanced osteoinductive composition 808 can then undergo a rehydration procedure to form a rehydrated enhanced osteoinductive composition 810. The rehydrated enhanced osteoinductive composition 810 can be malleable, soft, and/or can have the "cotton-like" texture and/or form factor, such that the rehydrated enhanced osteoinductive composition 810 can be manipulated and/or torn apart into a desired shape and/or size. The system 200 depicted in FIGS. 8A and 8B can be similar to and/or can form at least a portion of any of the system(s) 200 disclosed herein.

FIG. 9 shows an example system 200 including an enhanced DBM putty 902 composed of size-optimized DBM 904 and a growth factor peptide gel 906. The enhanced DBM putty 902 can undergo a freeze-drying procedure to form a freeze-dried enhanced DBM putty 908 with increased rigidity. Moreover, the freeze-dried enhanced DBM putty 908 can undergo a rehydration procedure to form a rehydrated enhanced DBM putty 920 with increased malleability. The system 200 depicted in FIG. 9 can be similar to and/or can form at least a portion of any of the system(s) 200 disclosed herein.

FIG. 10 shows an example system 200 including an enhanced osteoinductive composition 1002 composed of growth factor peptide 1004. In some examples, the enhanced osteoinductive composition 1002 can be freeze dried to form a growth factor peptide foam 1006. The growth factor peptide foam 1006 can be used as-is and/or can be at least partially rehydrated prior to use. The system 200 depicted in FIG. 10 can be similar to and/or can form at least a portion of any of the system(s) 200 disclosed herein.

FIG. 11 shows an example system 200 including an enhanced DBM putty 1102 composed of sized-optimized DBM particles 904 and a phospholipid carrier 1104. The system 200 depicted in FIG. 11 can be similar to and/or can form at least a portion of any of the system(s) 200 disclosed herein.

EXAMPLE INSTANCES

Disclosed example instances describe systems 200 and methods of conducting a size-optimized demineralization process 202 and compositions using the enhanced DBM particles created by these methods.

Example instance 1: A method of demineralizing bone wherein the bone particles are separated into two or more size ranges and demineralized independently using different demineralization parameters.

Example instance 2: A method including example instance 1, wherein the independent demineralization processes use longer demineralization times for larger particles and shorter demineralization times for smaller particles.

Example instance 3: A method including example instance 1, wherein the independent demineralization processes use higher acid concentrations for larger particles and lower acid concentrations for the smaller particles.

Example instance 4: A method including example instance 1, wherein the independent demineralization processes utilize stronger acids for larger particles and weaker acids for the smaller particles.

Example instance 5: A method including example instance 1, wherein the smallest and largest bone particles sizes are within <400 μm, <200 μm, or <150 μm of each other.

Example instance 6: A method including example instance 1, wherein the resultant demineralized bone matrix particles are subjected to additional size reduction processes to create particle sizes <125 μm.

Example instance 7: A method including example instance 1, wherein the size ranges comprise two or more of the following: <90 μm, <125 μm, 90-212 μm, 212-355 μm, 355-500 μm, 500-600 μm, 600-710 μm, or 710 μm-850 μm.

Example instance 8: A method including example instances 1 to 7, further comprising cryomilling an initial portion of cortical bone material to form the bone particles, the cryomilling comprising cryomilling at <0° C. temperatures by using liquid nitrogen, dry ice, or a freezer, or any combination thereof.

Example instance 9: Enhanced demineralized bone matrix (DBM) composition produced from a size-optimized demineralization process 202 wherein the bone particles are separated into at least two different size ranges and demineralized independently using different demineralization parameters.

Example instance 10: The enhanced demineralized bone matrix (DBM) composition of Example instance 9, wherein each size range is independently selected from the group consisting of <90 μm, <125 μm, 90 μm to less than 212 μm, 212 μm to less than 355 μm, 355 μm to less than 500 μm, 500 μm to less than 600 μm, 600 μm to less than 710 μm, and 710 μm to less than 850 μm.

Example instance 11: The enhanced demineralized bone matrix (DBM) composition of Example instance 9, wherein the at least two different size ranges comprise at least one size range of <125 μm.

Example instance 12: A tissue repair composition comprising enhanced demineralized bone matrix (DBM) composition from example instance 9, 10, or 11 and a biocompatible carrier.

Example instance 13: A tissue repair composition comprising the enhanced demineralized bone matrix (DBM) composition from example instance 9, 10, or 11 combined with a biocompatible carrier to create a moldable putty.

Example instance 14: A tissue repair composition comprising the enhanced demineralized bone matrix (DBM) composition from example instance 9, 10, or 11 combined with a biocompatible carrier to create an extrudable gel.

Example instance 15: A tissue repair composition comprising enhanced demineralized bone matrix (DBM) composition from example instance 9, 10, or 11 combined with a biocompatible carrier to create a flexible sheet.

Example instance 16: A tissue repair composition comprising osteoinductive demineralized bone matrix with a particle size range of <125 μm, <53 μm, or <25 μm.

Example instance 17: A bone contacting implant, wherein the surface of the bone contacting implant comprises the enhanced demineralized bone matrix (DBM) composition from example instance 9, 10, or 11.

Example instance 18: A liquid osteoinductive coating comprising enhanced demineralized bone matrix (DBM) composition from example instance 9, 10, or 11 and an aqueous solution.

Example instance 19: A liquid osteoinductive coating of Example instance wherein the aqueous solution comprises water, a hydrogel, a polymer solution, or a phospholipid solution, or any combination thereof.

Example instance 20: A bone implant comprising a bone contacting implant and the liquid osteoinductive coating of example instance 19.

Example instance 21: A bone implant of Example instance 20, wherein the liquid osteoinductive coating is dried causing the osteoinductive DBM particles to adhere to a surface of the porous bone contacting implant.

Example instance 22: A tissue repair composition comprising an osteoinductive fine particle DBM with a particle size <125 μm.

Example instance 23: A method of forming a tissue repair composition comprising separating bone particles into at least a first size range and a second size range; forming a size-optimized demineralized bone matrix (DBM) by independently demineralizing the bone particles of the first size range and the bone particles of the second size range by using a different demineralization parameter for the first size range than is used for the second size range; and combining the DBM with a biocompatible carrier to create the tissue repair composition.

Example instance 24: The method of Example instance 23 wherein the first size range is <125 μm; and the method further comprises producing an osteoinductive growth factor peptide powder from the bone particles in the first size range by: treating the bone particles in the first size range to convert collagen into gelatin; and subsequently drying the bone particles in the first size range to form the osteoinductive growth fact peptide powder.

Example instance 25: The method of Example instance 23 wherein the first size range is <125 μm, and the method further comprises producing a growth factor peptide solution from the demineralized bone particles of the first size range by: demineralizing the demineralized bone particles of the first size range in a demineralization solution to form a processed demineralization solution, and subjecting the processed demineralization solution to a protein isolation process to create a growth factor solution.

Example instance 26: A method of example instance 1, wherein the demineralization solution is subjected to a protein isolation process to create a growth factor solution.

Example instance 27: A method of example instance 25 or 26, wherein the protein isolation process utilizes dialysis, diafiltration, and/or precipitation methods.

Example instance 28: A method of example instance 25 or 26, wherein the protein isolation process utilizes dialysis or diafiltration with a molecular weight cutoff of 10 kDa or less.

Example instance 29: A growth factor powder produced by freeze-drying the growth factor solution produced by a method of example instance 26.

Example instance 30: The method of Example instance 26 further comprising creating an osteoinductive growth factor peptide powder by drying the growth factor peptide solution to create the growth factor peptide power.

Example instance 31: The method of Example instance 30 further comprising mixing the bone particles of the first size range with the growth factor peptide powder.

Example instance 32: The method of Example instance 31 wherein the tissue repair composition is freeze-dried to a rigid form that is designed to be inserted into a musculoskeletal implant.

Example instance 33: A tissue repair composition that combines the osteoinductive growth factor powder from example instance 29 with size-optimized demineralized bone matrix.

Example instance 34: A growth factor peptide powder that is produced from a fine particle DBM (<125 μm) from example instance 22 that is further treated to solubilize growth factors and fully or partially convert collagen into gelatin and is subsequently freeze-dried.

Example instance 35: A tissue repair composition, wherein the fine particle DBM from example instance 22 is mixed with a freeze-dried growth factor powder from example instance 29 and/or the growth factor peptide powder from example instance 34.

Example instance 36: A method of forming a soluble growth factor peptide solution, wherein cortical bone is milled to a particle size of <125 μm, the cortical bone powder (125 μm) is demineralized through a first process, a second demineralization process is conducted, and a soluble growth factor peptide solution is isolated through protein purification process.

Example instance 37: The method of Example instance 36 wherein the protein purification process comprises a dialysis process or a diafiltration process with a molecular cut off of 10 kDa or less.

Example instance 38: The method of example instance 36 or 37 further comprising drying the soluble growth factor peptide solution to form a growth factor peptide powder.

Example instance 39: A soluble growth factor peptide solution formed using a method of example instance 36 or 37.

Example instance 40: A growth factor peptide powder formed using a method of example instance 38.

Example instance 41: A tissue repair composition comprising the growth factor peptide solution of example instance 39; and cortical bone particles, cancellous bone particles, DBM particles, and/or DBM fibers; wherein the growth factor peptide solution, growth factor peptide powder, cortical bone particles, cancellous bone particles, DBM particles, and/or DBM fibers are all derived from the same tissue donor.

Example instance 42: A tissue repair composition comprising the growth factor peptide powder of example instance 40; and cortical bone particles, cancellous bone particles, DBM particles, and/or DBM fibers; wherein the growth factor peptide solution, growth factor peptide powder, cortical bone particles, cancellous bone particles, DBM particles, and/or DBM fibers are all derived from the same tissue donor.

Example instance 43: A liquid osteoinductive coating comprising soluble growth factor peptide solution of Example instance 39 and an aqueous solution.

Example instance 44: A liquid osteoinductive coating comprising the growth factor peptide powder of Example instance 40 and an aqueous solution.

Additional Examples of Manufacture

The following non-limiting additional examples of manufacture are provided for illustrative purposes to facilitate a more complete understanding of the representative example instances. These examples should not be construed to limit any of the example instances described in the present specification. In the following descriptions, a size-optimized demineralization process 202, a fine particle milling process, a growth factor peptide process, and various tissue repair compositions using the same are described for such illustrative purposes.

A first example (e.g., "Example 1") of the technology disclosed herein can include enhanced DBM created from a size-optimized demineralization process 202.

For instance, cortical bone powder from a single tissue donor can be created using standard tissue bank harvesting, cleaning, defatting, and grinding techniques to produce particles having a size range of <850 μm. The ground bone was placed on an 850 μm sieve located at the top of a sieve stack with the size ranges indicated in Table 1. The sieves were agitated using a mechanical sieve shaker to separate the bone particles into the various size ranges. Weight measurement of the size ranges resulted in the size distribution shown in FIG. 5. Following sieving, seven separate size ranges were created. The bone particles were weighed, placed in seven separate containers, and 0.5 N HCl was added in a ratio of 1 g of bone per 10 ml of 0.5 N HCl. The bone/acid suspensions were stirred using a magnetic stir bar for the size specific demineralization times found in Table 1. Once the demineralization time was reached for each size, the acid demineralization solution was removed by vacuum filtration. The DBM particles were then neutralized to a pH of 7-8 with a 1 M sodium hydroxide solution. DBM particles were vacuum filtered again and rinsed with water. Once all demineralization processes were completed for each size range, the wet DBM was freeze-dried. Alternatively, the wet DBM from each size range can be combined into a single bulk amount and freeze-dried together to remove the water. The DBM produced from this process can then be used to create enhanced osteoinductive compositions.

A second example (e.g., "Example 2") of the technology disclosed herein can include fine particle DBM specifically created from a small cortical bone particle size range (e.g., <125 μm).

For instance, cortical bone powder from a single tissue donor was created using standard tissue banking harvesting, cleaning, defatting, and grinding techniques. This resulted in a broad 125-850 μm size range. The cortical bone powder was then be processed on a cryomill to reduce the particle size to <125 μm. Due to the capacity of the cryomill, the cortical bone donor lot was separated into 30 g sub-batches. Each sub-batch was cryomilled using a 15 minute pre-cooling cycle followed 5 milling cycles (2 min milling and 2 min cooling). Following milling, the sub-batches were be recombined into a single bulk amount. An example of the cortical bone before and after cryomilling in shown in FIG. 6. The milled bone powder was then placed in a large container and 0.5 N HCl was added in a ratio 1 g of bone per 10 ml of 0.5 N HCl. The bone/acid suspension was mixed with an overhead paddle stirrer for 15 minutes. Following demineralization, the DBM was isolated from the acid solution using vacuum filtration. Once the HCl solution was removed, the DBM was neutralized with 1 M NaOH (pH 7-8), rinsed with water, vacuum filtered, and freeze-dried. Following freeze-drying, the fine particle DBM powder was lightly ground to break apart the particle clumps until a free flowing <125 μm powder was obtained. The small particle DBM powder produced from this process can then be used to create enhanced osteoinductive compositions or coatings.

A third example (e.g., "Example 3") of the technology disclosed herein can include growth factor peptide created from fine from fine particle DBM <125 μm.

For instance, the fine particle DBM from Example 2 can be subjected to a second demineralization step to solubilize growth factors from the DBM particles and create soluble collagen (gelatin and/or hydrolyzed collagen). In this process, the fine particle DBM was combined with 3M citric acid in a 1 g DBM to 20 ml acid ratio. The mixture was stirred with an overhead mechanical stirrer for 48 hrs. Following mixing, the solution was centrifuged to form a residual DBM pellet and acidic growth factor peptide solution supernatant. The supernatant solution was isolated from the pellet. The residual DBM pellet was rinsed with water and the water rinse was added to the supernatant. The residual DBM pellet can be saved for further processing or inclusion in osteoinductive compositions, or it can be discarded. The isolated growth factor peptide solution was then neutralized using 1 M NaOH (pH 7-8). The neutralized growth factor peptide solution was then desalted using a tangential flow filter with a 5 kDa molecular weight cut-off membrane. Following desalting, the growth factor peptide solution was freeze-dried. This resulted in the formation a cotton-like material. This is shown in FIG. 7.

A fourth example (e.g., "Example 4") of the technology disclosed herein can include an enhanced osteoinductive composition created from sized optimized DBM fibers and growth factor peptide.

For instance, a portion of the freeze-dried growth factor peptide material from Example 3 was used to create a coating on DBM fibers. In this process, a 2.5% (g/ml) solution of the growth factor peptide was created with the addition of water. Once fully solubilized, the growth factor peptide solution was added to dry DBM fibers in a ratio of 5 ml of solution to 1 g of DBM fibers. This caused the dry fibers to rehydrate, absorb some of the growth factor peptide solution, and become flexible. Following rehydration, the mixture was freeze-dried which resulted in an osteoinductive composition consisting of DBM fibers embedded in a growth factor peptide foam. This is shown in FIG. 8A. As shown in the images, this composition can be designed to be rehydrated at the time of surgery to revert back to a flexible form. This is shown in FIG. 8B.

A fifth example (e.g., "Example 5") of the technology disclosed herein can include an osteoinductive composition involving enhanced DBM putty created from the combination of sized optimized DBM and growth factor peptide that has the ability to form a gel.

This initially involves the split of ground cortical bone into a first portion of cortical bone subjected to the sized optimized demineralization of Example 1 and a second portion of cortical bone that can be cryomilled according to Example 2 and then formed into growth factor peptide according to Example 3. For instance, the growth factor peptide was reconstituted with water to form an 8% (g/ml) mixture that was capable of forming a gel. The gel was refrigerated to accelerate the process. Once gelled, size optimized DBM from example 1 was added to create a DBM putty mixture. This is shown in FIG. 9. The DBM putty mixture was then freeze-dried to create a form that can be designed to be rehydrated at the time of surgery. Alternatively, the DBM putty can be provided in a pre-hydrated form.

A sixth example (e.g., "Example 6") of the technology disclosed herein can include a freeze-dried osteoinductive composition designed to function as an insert into orthopedic and spinal implants.

For instance, the enhanced DBM putty of Example 5 was freeze dried in a rod form to function as an insert in a cannulated screw. Following freeze-drying, the insert had a rigid form that could be easily slipped into the open cannula area of the screw. In this example, the growth factor peptide functioned as a "glue" that bound the DBM particles together in a rod form that matched the inner dimensions of the cannulated screw.

A seventh example (e.g., "Example 7") of the technology disclosed herein can include an osteoinductive composition composed solely of growth factor peptide.

For instance, the freeze-dried growth factor peptide from Example 3 was solubilized in water to create 2.5% (g/ml) solution. A 2.5 ml volume of the 2.5% solution was added to a product container and freeze dried directly within the container. This resulted in a growth factor peptide foam. This is shown in FIG. 10. This foam can be designed to be rehydrated during surgery and can be combined with other graft materials or used as a coating on porous implants.

A eighth example (e.g., "Example 8") of the technology disclosed herein can include an osteoinductive composition involving enhanced DBM putty.

For instance, the enhanced DBM particles from Example 1 were combined with a moldable phospholipid carrier to create an enhanced DBM Putty. The enhanced DBM putty consisted of 35% DBM (by weight) and 65% carrier (by weight). The resulting mixture showed acceptable putty moldability, cohesiveness, and handling. This is shown in FIG. 11.

A sixth (e.g., "Example 6") of the technology disclosed herein can include an osteoinductive composition involving an osteoinductive coating.

For instance, the fine particle DBM powder from Example 2 can be used to form a coating for a porous ceramic bone graft. This can be done by mixing the fine particle DBM powder with an aqueous carrier to create a flowable slurry. For example, a carrier solution can be formed using a 10% mixture of Pluronic F127 in 4° C. chilled water. Pluronic solutions can be thermo-reversible whereby they have a low viscosity at lower temperatures and a higher viscosity at higher temperatures. A liquid OI coating can be formed by mixing 15% (w/w) fine particle DBM powder from Example 2 with 85% (w/w) Pluronic F127 solution. The mixture can be kept refrigerated to maintain the low viscosity. Porous, synthetic bone graft granules (e.g., 1-3 mm) can be added to the chilled slurry until the granules are completely saturated with slurry and the granules remain fully submerged/coated in the slurry mixture. The mixture can then be subjected to room temperature vacuum cycling (e.g., with the vacuum added and released) to pull the slurry into the entire porosity of the mixture. Once the granules are fully coated/impregnated, they can be removed from the excess coating solution, spread out on a drying tray, and allowed to dry for 72 hours. Once fully dried, the coated granules can be gently broken apart and re-sieved to granule size range (e.g., 1-3 mm). This can result in synthetic bone graft granules with a dried osteoinductive coating.

A summary of these examples and other examples is outlined in FIGS. 12 and 13. These flowcharts depict example method(s) including various operations for forming one or more compositions from an enhanced DBM generation procedure.

For instance, as shown in FIG. 12, one or more method(s) 1200 performed with the system(s) 200 disclosed herein can include multiple operations such as providing cortical bone particles or fibers and performing a size optimized demineralization process, which can optionally include cryomilling the cortical bone particles to produce a greater quantity of <125 µm particles. The method(s) 1200 can also include forming an enhanced DBM with particle sizes between 125-850 µm; performing a protein isolation procedure on the demineralization solution; forming a fine power DBM with particle sizes of <125 µm; and/or forming a growth factor peptide from fine particle DBM with particles sizes <125 µm. These operations can be performed in parallel. Moreover, the method(s) 1200 can include adding the enhanced DBM to a bone graft carrier to form a first tissue repair composition (Composition #1) comprising an enhanced DBM putty, gel and/or sheet. Additionally, or alternatively, the enhanced DBM can in itself form a second tissue repair composition (Composition #2) of an enhanced DBM particle or fiber product. Furthermore, the protein isolation can be freeze-dried to form a growth factor powder, which can be combined with the enhanced DBM to form a third tissue repair composition (Composition #3). Also, the fine particle DBM can be processed into a growth factor peptide, which can be freeze-dried and combined with enhanced DBM particles or fibers to form a fourth tissue repair composition (Composition #4).

Turning to FIG. 13, one or more method(s) 1300 performed with the system(s) 200 disclosed herein can further include cryomilling the cortical bone particles to form fine particle cortical bone with a size of <125 µm. These particles can undergo an optimized demineralization process to form a fine particle DBM (e.g., with particles being <125 µm) and/or a protein isolation from the demineralization solution. The fine particle DBM can in itself form a fifth tissue repair composition (Composition #5), and/or the fine particle DBM can be combined with freeze-dried growth factor powder from the protein isolation to form a sixth tissue repair composition (Composition #6). Additionally, or alternatively, a portion of the fine particle DBM can be processed into a growth factor peptide, which can be combined with fine particle DBM (Composition #5) to form a seventh tissue repair composition (Composition #7). The freeze-dried growth factor peptide can, in itself, form an eighth tissue repair composition (Composition #8). Moreover, another portion of the fine particle DBM can be mixed with an aqueous solution to form a coating. This coating can be mixed with a porous bone contacting implant and can be freeze-dried to form a ninth tissue repair composition (Composition #9) comprising an osteoinductive coated implant. The ninth tissue repair composition can be combined with the freeze-dried growth factor powder from the protein isolation to form a tenth tissue repair composition (Composition #10) comprising the osteoinductive coated implant (Composition #9) combined with the growth factor powder.

It is to be understood that the specific order or hierarchy of steps in the method(s) 1200 and 1300 of this disclosure are instances of example approaches and can be rearranged while remaining within the disclosed subject matter. For instance, any of the operations discussed throughout this disclosure may be omitted, repeated, performed in parallel, performed in sequence, performed in a different order, and/or combined with any other of the operations of this disclosure.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined differently in various implementations of the disclosure or described with different terminology. Any of the components or steps disclosed herein can be duplicated, omitted, and/or combined with any other components or steps disclosed herein. These and other variations, modifications, additions, and improvements may fall within the scope of the disclosure as defined in the claims that follow.

What is claimed is:

1. A method of forming soluble growth factor peptide solution, the method comprising:

milling or cryomilling cortical bone to a particle size range of <125 µm to form a cortical bone powder;

demineralizing the cortical bone powder through a first primary demineralization process comprising soaking the cortical bone powder for <30 minutes in a solution comprising 0.2 N to 1.0 N HCl to form a primary demineralized cortical bone mass;

conducting a second demineralizing on the primary demineralized cortical bone mass comprising soaking the primary demineralized cortical bone mass in 2 M to 4 M citric acid for a period of time to obtain a secondary demineralized bone mass and a demineralization supernatant; and isolating a soluble growth factor peptide solution from the demineralization supernatant through a protein purification process.

2. The method of claim 1, wherein the protein purification process comprises a dialysis process or a diafiltration process with a molecular weight cut off of 10 kDa or less.

3. The method of claim 1, further comprising drying the soluble growth factor peptide solution to form a growth factor peptide powder.

* * * * *